(12) United States Patent
Hebeisen et al.

(10) Patent No.: US 7,781,593 B2
(45) Date of Patent: *Aug. 24, 2010

(54) 5-PHENYL-NICOTINAMIDE DERIVATIVES

(75) Inventors: Paul Hebeisen, Basel (CH); Stephan Roever, Inzlingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 165 days.

This patent is subject to a terminal disclaimer.

(21) Appl. No.: 11/846,667

(22) Filed: Aug. 29, 2007

(65) Prior Publication Data

US 2008/0070931 A1 Mar. 20, 2008

(30) Foreign Application Priority Data

Sep. 14, 2006 (EP) .................................. 06120672

(51) Int. Cl.
C07D 213/82 (2006.01)
(52) U.S. Cl. ...................................... 546/316; 514/355
(58) Field of Classification Search .................. 546/316
See application file for complete search history.

(56) References Cited

U.S. PATENT DOCUMENTS

| 3,940,418 | A | 2/1976 | Hamilton |
| 5,462,960 | A | 10/1995 | Barth et al. |
| 5,596,106 | A | 1/1997 | Cullinan et al. |
| 5,624,941 | A | 4/1997 | Barth et al. |
| 6,028,084 | A | 2/2000 | Barth et al. |
| 6,355,631 | B1 | 3/2002 | Achard et al. |
| 6,432,984 | B1 | 8/2002 | Barth et al. |
| 6,479,479 | B2 | 11/2002 | Achard et al. |
| 6,509,367 | B1 | 1/2003 | Martin et al. |
| 6,566,356 | B2 | 5/2003 | Achard et al. |
| 6,645,985 | B2 | 11/2003 | Barth et al. |
| 6,734,176 | B2 | 5/2004 | Achard et al. |
| 6,872,717 | B2 | 3/2005 | Achard et al. |
| 6,893,659 | B2 | 5/2005 | Abramovici et al. |
| 6,906,080 | B1 | 6/2005 | Barth et al. |
| 7,037,944 | B2 | 5/2006 | Piot-Grosjean et al. |
| 7,132,414 | B2 | 11/2006 | Achard et al. |
| 7,148,258 | B2 | 12/2006 | Piot-Grosjean et al. |
| 7,229,999 | B2 | 6/2007 | Hebeisen et al. |
| 2001/0027193 | A1 | 10/2001 | Achard et al. |
| 2002/0019383 | A1 | 2/2002 | Achard et al. |
| 2002/0091114 | A1 | 7/2002 | Piot-Grosjean et al. |
| 2002/0188007 | A1 | 12/2002 | Barth et al. |
| 2003/0003145 | A1 | 1/2003 | Abramovici et al. |
| 2003/0055033 | A1 | 3/2003 | Achard et al. |
| 2003/0119810 | A1 | 6/2003 | Achard et al. |
| 2004/0039024 | A1 | 2/2004 | Barth et al. |
| 2004/0157823 | A1 | 8/2004 | Achard et al. |
| 2004/0192667 | A1 | 9/2004 | Makriyannis et al. |
| 2004/0259887 | A1 | 12/2004 | Dow |
| 2005/0032773 | A1 | 2/2005 | Piot-Grosjean et al. |
| 2005/0032774 | A1 | 2/2005 | Piot-Grosjean et al. |
| 2005/0130953 | A1 | 6/2005 | Achard et al. |
| 2005/0192332 | A1 | 9/2005 | Barth et al. |
| 2006/0189664 | A1 | 8/2006 | Barth et al. |
| 2006/0258709 | A1 | 11/2006 | Piot-Grosjean et al. |
| 2007/0293509 | A1 | 12/2007 | Hebeisen et al. |
| 2008/0085905 | A1 | 4/2008 | Dietz et al. |
| 2008/0085906 | A1 | 4/2008 | Andjelkovic et al. |

FOREIGN PATENT DOCUMENTS

| EP | 576357 | 12/1993 |
| EP | 656354 | 6/1995 |
| EP | 658546 | 6/1995 |
| FR | 2856684 | 12/2004 |
| FR | 2 876 691 | 4/2006 |
| WO | WO 96/02248 | 2/1996 |
| WO | WO 97/19063 | 5/1997 |
| WO | WO 98/31227 | 7/1998 |
| WO | WO 98/41519 | 9/1998 |
| WO | WO 98/43635 | 10/1998 |
| WO | WO 98/43636 | 10/1998 |
| WO | WO 00/15609 | 3/2000 |
| WO | WO 00/46209 | 8/2000 |
| WO | WO 01/32663 | 5/2001 |
| WO | WO 01/64632 | 9/2001 |
| WO | WO 01/64633 | 9/2001 |
| WO | WO 01/64634 | 9/2001 |

(Continued)

OTHER PUBLICATIONS

Krishnamurthy et. al. "Synthesis, biological evaluation, and structural studies on N1 and C5 substituted cycloalkyl analogues of the pyrazole class of CB1 and CB2 ligands" Bioorganic & Medicinal Chemistry 12 (2004) 393-404.*

(Continued)

*Primary Examiner*—Janet L. Andres
*Assistant Examiner*—David K O'Dell
(74) *Attorney, Agent, or Firm*—George W. Johnston; Dennis P. Tramaloni

(57) ABSTRACT

The present invention relates to compounds of the formula

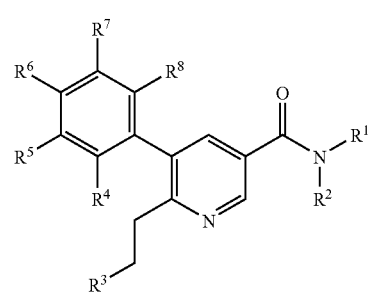

wherein $R^1$ to $R^8$ are as defined in the description and claims, and pharmaceutically acceptable salts thereof. The compounds are useful for the treatment and/or prophylaxis of diseases which are associated with the modulation of CB1 receptors.

20 Claims, No Drawings

FOREIGN PATENT DOCUMENTS

| | | |
|---|---|---|
| WO | WO 01/70700 | 9/2001 |
| WO | WO 02/28346 | 4/2002 |
| WO | WO 03/051850 | 6/2003 |
| WO | WO 03/051851 | 6/2003 |
| WO | WO 03/082191 A2 | 10/2003 |
| WO | WO 03/084930 | 10/2003 |
| WO | WO 2004/099157 | 11/2004 |
| WO | WO 2004/110453 | 12/2004 |
| WO | WO 2004/111033 | 12/2004 |
| WO | WO 2004/111034 | 12/2004 |
| WO | WO 2004/111039 | 12/2004 |
| WO | WO 2004111038 | 12/2004 |
| WO | WO 2005/016286 | 2/2005 |
| WO | WO 2005/074939 | 8/2005 |
| WO | WO 2005/075440 | 8/2005 |
| WO | WO 2005/075464 | 8/2005 |
| WO | WO 2005/080342 | 9/2005 |
| WO | WO 2005/080349 | 9/2005 |
| WO | WO 2005/080350 | 9/2005 |
| WO | WO 2005/115987 | 12/2005 |
| WO | WO 2006/042955 | 4/2006 |
| WO | WO 2006/046778 | 5/2006 |
| WO | WO 2006/106054 | 10/2006 |
| WO | WO 2007/147746 | 12/2007 |

OTHER PUBLICATIONS

Shankar et. al. "Triaryl bis-sulfones as cannabinoid-2 receptor ligands: SAR studies 3." Bioorganic & Medicinal Chemistry Letters 15 (2005) 4417-4420.*
Lu et. al. "Adamantyl Cannabinoids: A Novel Class of Cannabinergic Ligands" Journal of Medicinal Chemistry 2005, 48, 4576-4585.*
Pacheco et al., J. Pharmacol. Exp. Ther., 257(1), pp. 170-183 (1991).
Casiano et al., NIDA Res. Monogr., 105, pp. 295-296 (1991).
Hosohata et al., Life Sci., 61, pp. 115-118 (1997).
Pertwee et al., Life Sci., 56(23-24), pp. 1949-1955 (1995).
Felder et al., J. Pharmacol. Exp. Ther., 284(1), pp. 291-297 (1998).
Kanyonyo et al., Bioorg. Med. Chem. Lett. 9(15), pp. 2233-2236 (1999).
Ooms et al., J. Med. Chem., 45(9), pp. 1748-1756 (2002).
Barth et al., "*Cannabinoid Antagonists; From Research Tools to Potential New Drugs*", Abstracts of Papers, 222$^{nd}$ ACS National Meeting, Chicago, IL, USA, Aug. 26-30, 2001.
Barth et al., "*Cannabinoid Antagonists: From Research Tools to Potential New Drugs*", Abstracts of Papers, 222$^{nd}$ ACS National Meeting, Chicago, IL, USA, Aug. 26-30, 2001.
Gaoni et al., J. Am. Chem. Soc., 86, pp. 1646-1647 (1964).
Mechoulam, R., (Ed.) "*Cannabinoids As Therapeutic Agents*" pp. 1-19 (1986) (CRC Press).
Pertwee, R.G., Pharmaceut. Sci., 3, pp. 539-545 (1997).
Williamson et al., Drugs, 60, pp. 1301-1314 (2000).
Pertwee, R.G., Curr. Med. Chem., 6, pp. 535-664 (1999).
Devane et al., Science, 258, pp. 1946-1949 (1992).
Di Marzo et al., Trends in Neuroscience, 21, pp. 521-528 (1998).
Porter et al., Pharmacol. Ther., 90, pp. 45-60 (2001).
Williams et al., Psychopharmacology, 143, pp. 315-317 (1999).
Felder et al., Proc. Natl. Acad. Sci. USA, 90, pp. 7656-7660 (1993).
Colombo et al., Life Sci., 63, pp. L113-L117 (1998).
U.S. Appl. No. 12/404,364, Hebeisen et al.
U.S. Appl. No. 12/404,365, Hebeisen et al.

* cited by examiner

5-PHENYL-NICOTINAMIDE DERIVATIVES

PRIORITY TO RELATED APPLICATION(S)

This application claims the benefit of European Patent Application No. 06120672.8, filed Sep. 14, 2006, which is hereby incorporated by reference in its entirety.

BACKGROUND OF THE INVENTION

The present invention relates to novel 5-phenyl-nicotinamide derivatives, their manufacture, pharmaceutical compositions containing them and their use as medicaments. The active compounds of the present invention are useful in treating diseases associated with the modulation of CB1 receptors.

Two different subtypes of cannabinoid receptors ($CB_1$ and $CB_2$) have been isolated and both belong to G protein coupled receptor superfamily. Alternative spliced forms of $CB_1$, $CB_{1A}$ and $CB_{1B}$ have also been described, but are expressed only at low levels in the tissues tested. (D. Shire, C. Carrillon, M. Kaghad, B. Calandra, M. Rinaldi-Carmona, G. Le Fur, D. Caput, P. Ferrara, J. Biol. Chem. 270 (8) (1995) 3726-31; E. Ryberg, H. K. Vu, N. Larsson, T. Groblewski, S. Hjorth, T. Elebring, S. Sjögren, P. J. Greasley, FEBS Lett. 579 (2005) 259-264). The $CB_1$ receptor is mainly located in the brain and to a lesser extent in several peripheral organs, whereas the $CB_2$ receptor is predominately distributed in the periphery primarily localized in spleen and cells of the immune system (S. Munro, K. L. Thomas, M. Abu-Shaar, Nature 365 (1993) 61-61). Therefore in order to avoid side effects a $CB_1$-selective compound is desirable.

$\Delta^9$-tetrahydrocannabinol ($\Delta^9$-THC) is the principal psychoactive compound in the Indian hemp (Y. Gaoni, R. Mechoulam, J. Am. Chem. Soc., 86 (1964) 1646), *cannabis sativa* (marijuana), and has medicinal uses (R. Mechoulam (Ed.) in "*Cannabinoids as therapeutic Agents*", 1986, pp. 1-20, CRC Press). $\Delta^9$-THC is a non-selective $CB_{1/2}$ receptor agonist and is available in the USA as dronabinol (Marinol®) for the alleviation of cancer chemotherapy-induced emesis (CIE) and the reversal of body weight loss experienced by AIDS patients through appetite stimulation. In the UK Nabolinone (LY-109514, Cesamet®), a synthetic analogue of $\Delta^9$-THC, is used for CIE (R. G. Pertwee, Pharmaceut. Sci. 3 (11) (1997) 539-545, E. M. Williamson, F. J. Evans, Drugs 60 (6) (2000) 1303-1314).

Anandamide (arachidonylethanolamide) was identified as the endogenous ligand (agonist) for $CB_1$ (R. G. Pertwee, Curr. Med. Chem., 6 (8) (1999) 635-664; W. A. Devane, L. Hanus, A. Breuer, R. G. Pertwee, L. A. Stevenson, G. Griffin, D. Gibson, A. Mandelbaum, A. Etinger, R. Mechoulam, Science 258 (1992) 1946-9). Anandamide and 2-arachidonoylglycerol (2-AG) modulate at the presynaptic nerve terminal negatively adenylate cyclase and voltage-sensitive $Ca^{2+}$ channels and activates the inwardly rectifying $K^+$ channel (V. Di Marzo, D. Melck, T. Bisogno, L. De Petrocellis, Trends in Neuroscience 21 (12) (1998) 521-8), thereby affecting neurotransmitter release and/or action, which decreases the release of neurotransmitter (A. C. Porter, C. C. Felder, Pharmacol. Ther., 90 (1) (2001) 45-60).

Anandamide as $\Delta^9$-THC also increases feeding through $CB_1$ receptor-mediated mechanism. $CB_1$ selective antagonists block the increase in feeding associated with administration of anandamide (C. M. Williams, T. C. Kirkham, Psychopharmacology 143 (3) (1999) 315-317; C. C. Felder, E. M. Briley, J. Axelrod, J. T. Simpson, K. Mackie, W. A. Devane, Proc. Natl. Acad. Sci. U.S.A. 90 (16) (1993) 7656-60) and cause appetite suppression and weight loss (G. Colombo, R. Agabio, G. Diaz, C. Lobina, R. Reali, G. L. Gessa, Life Sci. 63 (8) (1998) L113-PL117).

Leptin is the primary signal through which the hypothalamus senses nutritional state and modulates food intake and energy balance. Following temporary food restriction, CB1 receptor knockout mice eat less than their wild-type littermates, and the CB1 antagonist SR141716A reduces food intake in wild-type but not knockout mice. Furthermore, defective leptin signaling is associated with elevated hypothalamic, but not cerebellar, levels of endocannabinoids in obese db/db and ob/ob mice and Zucker rats. Acute leptin treatment of normal rats and ob/ob mice reduces anandamide and 2-arachidonoyl glycerol in the hypothalamus. These findings indicate that endocannabinoids in the hypothalamus may tonically activate CB1 receptors to maintain food intake and form part of the neural circuitry regulated by leptin (V. Di Marzo, S. K. Goparaju, L. Wang, J. Liu, S. Bitkai, Z. Jarai, F. Fezza, G. I. Miura, R. D. Palmiter, T. Sugiura, G. Kunos, Nature 410 (6830) 822-825).

At least two CB1 selective antagonists/inverse agonists (SR-141716 and SLV-319) are currently undergoing clinical trials for the treatment of obesity and/or smoking cessation. In a double blind placebo-controlled study, at the doses of 10 and 20 mg daily, SR 141716 significantly reduced body weight when compared to placebo (F. Barth, M. Rinaldi-Carmona, M. Arnone, H. Heshmati, G. Le Fur, "*Cannabinoid antagonists: From research tools to potential new drugs*." Abstracts of Papers, 222nd ACS National Meeting, Chicago, Ill., United States, Aug. 26-30, 2001). SR-141716 reduced body weight, waist circumference and improved metabolic parameters (plasma HDL, triglycerides and insulin sensitivity) in several phase III studies (RIO-lipids, RIO-Europe and RIO-North America). Additionally SR-141716 has shown efficacy in a phase III trial for smoking cessation (STRATUS-US).

Substituted pyrazoles having activity against the cannabinoid receptors are disclosed in U.S. Pat. Nos. 5,624,941, 6,028,084 and 6,509,367, in PCT patent applications WO 98/031227, WO 98/041519, WO 98/043636, WO 98/043635, WO 04/0099157, in U.S. patent application US 2004192667 A1 and in patent application EP 658546.

Substituted pyridines, pyrimidines and pyrazines having activity against the cannabinoid receptors are disclosed in US patent application US 04/0259887 and in PCT patent applications WO 03/051850, WO 03/051851, WO 03/084930, WO 04/110453, WO 04/111033, WO 04/111034, WO 04/111038, WO 04/111039, WO05/016286, WO05/074939, WO05/075440, WO05/075464, WO05/080342, WO05/080349, WO05/080350, WO05/115987, WO06/046778, WO06042955 and in patent applications FR 2856684 and FR 2876691.

Other compounds which have been proposed as CB1 receptor antagonists respectively inverse agonists are aminoalkylindols (AAI; M. Pacheco, S. R. Childers, R. Arnold, F. Casiano, S. J. Ward, J. Pharmacol. Exp. Ther. 257 (1) (1991) 170-183). Examples thereof are 6-bromo-(WIN54661; F. M. Casiano, R. Arnold, D. Haycock, J. Kuster, S. J. Ward, NIDA Res. Monogr. 105 (1991) 295-6) or 6-iodopravadoline (AM630, K. Hosohata, R. M. Quock, R. M; Hosohata, T. H. Burkey, A. Makriyannis, P. Consroe, W. R. Roeske, H. I. Yamamura, Life Sci. 61 (1997) 115-118; R. Pertwee, G. Griffin, S. Fernando, X. Li, A. Hill, A. Makriyannis, Life Sci. 56 (23-24) (1995) 1949-55). Furthermore, arylbenzo[b]thiophene and benzo[b]furan derivatives (LY320135, C. C. Felder, K. E. Joyce, E. M. Briley, M. Glass, K. P. Mackie, K. J. Fahey, G. J. Cullinan, D. C. Hunden, D. W. Johnson, M. O.

Chaney, G. A. Koppel, M. Brownstein, J. Pharmacol. Exp. Ther. 284 (1) (1998) 291-7) as disclosed in WO 96/02248 or U.S. Pat. No. 5,596,106, 3-alkyl-(5,5-diphenyl)imidazolidinediones (M. Kanyonyo, S. J. Govaerts, E. Hermans, J. H. Poupaert, D. M. Lambert, Bioorg. Med. Chem. Lett. 9 (15) (1999) 2233-2236.) as well as 3-alkyl-5-arylimidazolidinediones (F. Ooms, J. Wouters, O. Oscaro. T. Happaerts, G. Bouchard, P.-A. Carrupt, B. Testa, D. M. Lambert, J. Med. Chem. 45 (9) (2002) 1748-1756) are known to antagonize the $CB_1$ receptor respectively act as an inverse agonist on the $hCB_1$ receptor. In WO 00/15609 (FR2783246-A1), WO 01/64634 (FR2805817-A1), WO 02/28346, WO 01/64632 (FR2805818-A1) and WO 01/64633 (FR2805810-A1) are disclosed substituted 1-bis(aryl)methyl-azetidines derivatives as antagonists of $CB_1$. In WO 01/70700 4,5-dihydro-1H-pyrazole derivatives are described as $CB_1$ antagonists. In several patent documents bridged and non-bridged 1,5-diphenyl-3-pyrazolecarboxamide derivatives are disclosed as $CB_1$ antagonists/inverse agonists (WO 01/32663, WO 00/46209, WO 97/19063, EP 658546, EP 656354, U.S. Pat. No. 5,624,941, EP 576357 and U.S. Pat. No. 3,940,418). However, there still remains a need for potent low molecular weight CB1 modulators that have improved pharmacokinetic and pharmacodynamic properties suitable for use as human pharmaceuticals.

It is therefore an object of this invention to provide selective, directly acting CB1 receptor antagonists/inverse agonists. Such antagonists/inverse antagonists are useful in medical therapy, particularly in the treatment and/or prevention of diseases which are associated with the modulation of CB1 receptors.

SUMMARY OF THE INVENTION

The present invention relates to the compounds of the formula I and all pharmaceutically acceptable salts thereof wherein formula I is:

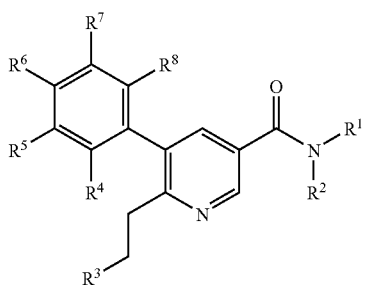

wherein $R^1$-$R^{13}$ are as defined in the detailed description and in the claims. Compounds of formula I of the present invention are modulators of the $CB_1$ receptor and are useful in the treatment of diseases which are associated with the $CB_1$ receptor.

DETAILED DESCRIPTION OF THE INVENTION

Unless otherwise indicated, the following definitions are set forth to illustrate and define the meaning and scope of the various terms used to describe the invention herein.

In this specification the term "lower" used in combination with a named group means a group or substituent consisting of one to seven carbon atom(s). In preferred embodiments a lower group has one to four carbon atom(s).

The term "alkyl", alone or in combination with other groups, refers to a branched or straight-chain monovalent saturated aliphatic hydrocarbon radical of one to twenty carbon atoms. In preferred embodiments the akyl has one to sixteen carbon atoms, more preferably one to ten carbon atoms.

The term "lower alkyl" or "$C_{1-7}$-alkyl", alone or in combination with other groups, refers to a branched or straight-chain monovalent alkyl radical of one to seven carbon atoms. In preferred embodiments the "lower alkyl" has one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "alkoxy" refers to the group R'—O—, wherein R' is alkyl. The term "lower alkoxy" or "$C_{1-7}$-alkoxy" refers to the group R'—O—, wherein R' is lower alkyl. Examples of lower alkoxy groups are, for example, methoxy, ethoxy, propoxy, isopropoxy, butoxy, isobutoxy and hexyloxy, with methoxy being especially preferred.

The term "lower alkoxyalkyl" or "$C_{1-7}$-alkoxy-$C_{1-7}$-alkyl" refers to a lower alkyl group as defined above which is mono- or multiply substituted with a lower alkoxy group as defined above. Examples of lower alkoxyalkyl groups are, for example, —$CH_2$—O—$CH_3$, —$CH_2$—$CH_2$—O—$CH_3$, —$CH_2$—O—$CH_2$—$CH_3$ and the groups specifically exemplified herein. Most preferably, lower alkoxyalkyl is methoxyethyl.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Preferred are $C_{3-7}$-hydroxyalkyl groups. Examples of lower hydroxyalkyl groups are 2-hydroxybutyl, 3-hydroxy-2,2-dimethylpropyl and the groups specifically exemplified herein.

The term "halogen" refers to fluorine, chlorine, bromine and iodine. Preferred "halogen" groups are fluorine and chlorine.

The term "lower halogenalkyl" or "halogen-$C_{1-7}$-alkyl" refers to lower alkyl groups which are mono- or multiply substituted with halogen, preferably with fluoro or chloro, most preferably with fluoro. Examples of lower halogenalkyl groups are, for example, —$CF_3$, —$CHF_2$, —$CH_2Cl$, —$CH_2CF_3$, —$CH(CF_3)_2$, —$CF_2$—$CF_3$ and the groups specifically exemplified herein.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluoromethoxy and chloromethoxy, with trifluoromethoxy being especially preferred.

The term "lower hydroxyhalogenalkyl" or "hydroxy-halogen-$C_{1-7}$-alkyl" refers to lower halogenalkyl groups as defined herein before which are additionally substituted with a hydroxy group. Examples of lower hydroxyhalogenalkyl groups are, for example, 3,3,3-trifluoro-2-hydroxy-propyl and the groups specifically exemplified herein.

The term "cycloalkyl" or "$C_{3-7}$-cycloalkyl" refers to a monovalent carbocyclic radical of three to seven carbon atoms. In preferred embodiments, the "cycloalkyl" has three to five carbon atoms. This term is further exemplified by radicals such as cyclopropyl, cyclobutyl, cyclopentyl, cyclohexyl and cycloheptyl, with cyclopropyl being especially preferred.

The term "lower cycloalkylalkyl" or "$C_{3-7}$-cycloalkyl-$C_{1-7}$-alkyl" refers to a lower alkyl group as defined above which is mono- or multiply substituted with a cycloalkyl group as defined above. Examples of lower cycloalkylalkyl groups are, for example, —$CH_2$-cyclopropyl, —$CH_2$—$CH_2$-cyclobutyl, —$CH_2$-cyclopentyl and the groups specifically exemplified herein.

The term "heteroaryl" refers to an aromatic 5- or 6-membered ring which can comprise one, two or three atoms selected from nitrogen, oxygen and/or sulphur. Examples of heteroaryl groups are, for example, furyl, pyridyl, pyrazinyl, pyrimidinyl, pyridazinyl, thienyl, isoxazolyl, thiazolyl, isothiazolyl, oxazolyl, imidazolyl, pyrazolyl, triazolyl, oxadiazolyl, oxatriazolyl, tetrazolyl, pentazolyl, and pyrrolyl. The heteroaryl group can optionally be mono- or disubstituted independently by lower alkyl or halogen. The term "heteroaryl" also includes bicyclic aromatic moieties having 9 to 10 ring atoms with 1 to 3 heteroatoms such as benzofuranyl, benzothiazolyl, indolyl, benzoxazolyl, quinolinyl, isoquinolinyl, benzimidazolyl, benzisoxazolyl, and benzothienyl. Preferred heteroaryl groups are isoxazolyl, pyridyl, pyrimidinyl, imidazolyl, triazolyl, and thiazolyl, wherein said groups can optionally be mono- or disubstituted independently by lower alkyl or halogen. More preferred heteroaryl groups are pyridyl, pyrimidinyl and thiazolyl, wherein said groups can optionally be mono- or disubstituted independently by lower alkyl or halogen. Especially preferred are pyrimidin-5-yl, pyridin-3-yl, pyridine-2-yl, 5-fluoro-pyridin-2-yl, pyridine-4-yl and thiazol-2-yl.

The term "lower heteroarylalkyl" or "heteroaryl-$C_{1-7}$-alkyl" refers to lower alkyl groups as defined above wherein at least one of the hydrogen atoms of the lower alkyl group is replaced by a heteroaryl group as defined above.

The term "pharmaceutically acceptable salts" embraces salts of the compounds of formula I with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In reference to a particular group or molecule, the term "substituted" refers to the fact that at least one of the hydrogen atoms of that group or molecule is replaced by some other substituent.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of about 0.1 mg to about 5,000 mg, preferably from about 0.1 mg to about 1,000 mg, more preferably from about 0.5 to 500 mg, and more preferably from about 1 mg to 100 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" means any compound selected from the group of compounds defined by the genus of the formula.

In detail, the present invention relates to the compounds of formula I:

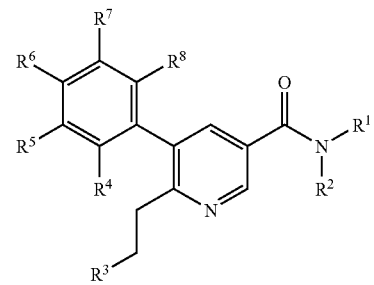

I and all pharmaceutically acceptable salts thereof, wherein:
(a) $R^1$ is selected from the group consisting of:
  (1) cycloalkyl which is optionally substituted by hydroxy or lower alkoxy,
  (2) lower hydroxyalkyl,
  (3) lower hydroxyhalogenalkyl,
  (4) —$CH_2$—$CR^9R^{10}$-cycloalkyl, wherein (i) $R^9$ is hydrogen or lower alkyl and (ii) $R^{10}$ is hydrogen, hydroxy or lower alkoxy; and
  (5) —$CR^{11}R^{12}$—$COOR^{13}$; wherein (i) $R^{10}$ is hydrogen, hydroxy or lower alkoxy; (ii) $R^{11}$ and $R^{12}$ independently from each other are hydrogen or lower alkyl; and (iii) $R^{13}$ is lower alkyl;
(b) $R^2$ is hydrogen;
(c) $R^3$ is selected from the group consisting of:
  (1) cycloalkyl,
  (2) lower cycloalkylalkyl,
  (3) lower alkoxy,
  (4) lower alkoxyalkyl,
  (5) halogen,
  (6) lower halogenalkyl,
  (7) phenyl, which is unsubstituted or mono-substituted or di-substituted independently by lower alkyl or halogen,
  (8) lower phenylalkyl, wherein said phenyl is unsubstituted or mono-substituted or di-substituted independently by lower alkyl or halogen,
  (9) heteroaryl, which is unsubstituted or mono-substituted or di-substituted independently by lower alkyl or halogen, and

(10) lower heteroarylalkyl, wherein the heteroaryl group is unsubstituted or mono-substituted or di-substituted independently by lower alkyl or halogen;

(d) $R^4$ and $R^8$ independently from each other are hydrogen or halogen;

(e) $R^5$ and $R^7$ independently from each other are selected from the group consisting of hydrogen, halogen, lower halogenalkyl, lower halogenoalkoxy, and cyano; and (f) $R^6$ is selected from the group consisting of hydrogen, halogen, lower halogenalkyl, lower halogenoalkoxy, and cyano.

Preferred are compounds of formula I as defined above, wherein $R^1$ is cycloalkyl which is unsubstituted or substituted by hydroxy or lower alkoxy, or —$CH_2$—$CR^9R^{10}$-cycloalkyl, wherein $R^9$ is hydrogen or lower alkyl and $R^{10}$ is selected from hydrogen, hydroxy and lower alkoxy.

Especially preferred are those compounds of formula I, wherein $R^1$ is cycloalkyl substituted by hydroxy. Most preferably, $R^1$ is cyclohexyl substituted by hydroxy.

Also preferred are compounds of formula I as defined above, wherein $R^1$ is —$CH_2$—$CR^9R^{10}$-cycloalkyl and wherein $R^9$ is hydrogen or lower alkyl and $R^{10}$ is selected from hydrogen, hydroxy and lower alkoxy. More preferably, $R^1$ is —$CH_2$—$CR^9R^{10}$-cycloalkyl wherein $R^9$ is methyl and $R^{10}$ is hydroxy. Most preferably, $R^1$ is —$CH_2$—$C(CH_3)OH$-cyclopropyl.

Preferred compounds of formula I according to the present invention are further those, wherein $R^3$ is selected from the group consisting of cycloalkyl, lower cycloalkylalkyl, lower alkoxy, lower alkoxyalkyl, heteroaryl which is unsubstituted or mono- or di-substituted independently by lower alkyl or halogen, and lower heteroarylalkyl, wherein the heteroaryl group is unsubstituted or mono- or di-substituted independently by lower alkyl or halogen.

More preferred are the compounds of formula I as defined above, wherein $R^3$ is selected from the group consisting of cycloalkyl, lower alkoxyalkyl and heteroaryl which is unsubstituted or mono- or di-substituted independently by lower alkyl or halogen.

Especially preferred are compounds of formula I as defined above, wherein $R^3$ is cycloalkyl.

Compounds of formula I, wherein $R^3$ is lower alkoxyalkyl, are also especially preferred.

Furthermore, compounds of formula I are especially preferred, wherein $R^3$ is heteroaryl which is unsubstituted or mono- or di-substituted independently by lower alkyl or halogen. More preferably, $R^3$ is heteroaryl selected from pyridyl, pyrimidinyl and thiazolyl, said heteroaryl being unsubstituted or mono- or di-substituted independently by lower alkyl or halogen. Most preferably, $R^3$ is selected from the group consisting of pyrimidin-5-yl, pyridin-3-yl, pyridine-2-yl, 5-fluoro-pyridin-2-yl, pyridine-4-yl and thiazol-2-yl.

Also preferred are compounds of formula I according to the present invention, wherein $R^4$ and $R^8$ independently from each other are hydrogen or halogen, $R^5$ and $R^7$ independently from each other are selected from the group consisting of hydrogen, halogen, lower halogenalkyl, lower halogenoalkoxy and cyano, $R^6$ is selected from the group consisting of hydrogen, halogen, lower halogenalkyl, lower halogenoalkoxy and cyano, and not all of $R^4$ to $R^8$ are hydrogen.

More preferably, compounds of formula I according to the invention are those, wherein $R^6$ is halogen or lower halogenalkyl and $R^4$, $R^5$, $R^7$ and $R^8$ are hydrogen.

Especially preferred are compounds of formula I, wherein $R^6$ is selected from the group of fluoro, chloro and trifluoromethyl.

Preferred compounds of formula I are the following compounds:

5-(4-chloro-phenyl)-N-((1R,2R)-2-hydroxy-cyclohexyl)-6-(3-methoxy-propyl)-nicotinamide, 5-(4-chloro-phenyl)-6-(2-cyclopropyl-ethyl)-N-((1R,2R)-2-hydroxy-cyclohexyl)-nicotinamide, N-((1R,2R)-2-hydroxy-cyclohexyl)-6-(2-pyrimidin-5-yl-ethyl)-5-(4-trifluoromethyl-phenyl)-nicotinamide, 5-(4-chloro-phenyl)-N—((R)-2-cyclopropyl-2-hydroxy-propyl)-6-(2-pyridin-3-yl-ethyl)-nicotinamide, 5-(4-fluoro-phenyl)-N-((1R,2R)-2-hydroxy-cyclohexyl)-6-(2-pyridin-3-yl-ethyl)-nicotinamide, 5-(4-fluoro-phenyl)-6-[2-(5-fluoro-pyridin-2-yl)-ethyl]-N-((1R,2R)-2-hydroxy-cyclohexyl)-nicotinamide, 5-(4-chloro-phenyl)-N-((1R,2R)-2-hydroxy-cyclohexyl)-6-(2-pyridin-3-yl-ethyl)-nicotinamide, 5-(4-chloro-phenyl)-N-((1R,2R)-2-hydroxy-cyclohexyl)-6-(2-pyridin-2-yl-ethyl)-nicotinamide, N-((1R,2R)-2-hydroxy-cyclohexyl)-6-(2-pyridin-3-yl-ethyl)-5-(4-trifluoromethyl-phenyl)-nicotinamide, N-((1R,2R)-2-hydroxy-cyclohexyl)-6-(2-pyridin-2-yl-ethyl)-5-(4-trifluoromethyl-phenyl)-nicotinamide, 5-(4-fluoro-phenyl)-N-((1R,2R)-2-hydroxy-cyclohexyl)-6-(2-pyridin-2-yl-ethyl)-nicotinamide, 5-(4-fluoro-phenyl)-N-((1R,2R)-2-hydroxy-cyclohexyl)-6-(2-pyridin-4-yl-ethyl)-nicotinamide, 5-(4-fluoro-phenyl)-N-((1R,2R)-2-hydroxy-cyclohexyl)-6-(2-thiazol-2-yl-ethyl)-nicotinamide, 5-(4-chloro-phenyl)-N-((1R,2R)-2-hydroxy-cyclohexyl)-6-(2-pyrimidin-5-yl-ethyl)-nicotinamide, 5-(4-chloro-phenyl)-6-[2-(5-fluoro-pyridin-2-yl)-ethyl]-N-((1R,2R)-2-hydroxy-cyclohexyl)-nicotinamide, 6-[2-(5-fluoro-pyridin-2-yl)-ethyl]-N-((1R,2R)-2-hydroxy-cyclohexyl)-5-(4-trifluoromethyl-phenyl)-nicotinamide, N—((R)-2-cyclopropyl-2-hydroxy-propyl)-5-(4-fluoro-phenyl)-6-(2-pyridin-4-yl-ethyl)-nicotinamide, N—((R)-2-cyclopropyl-2-hydroxy-propyl)-5-(4-fluoro-phenyl)-6-(2-thiazol-2-yl-ethyl)-nicotinamide, 5-(4-chloro-phenyl)-N—((R)-2-cyclopropyl-2-hydroxy-propyl)-6-(2-pyridin-2-yl-ethyl)-nicotinamide, N—((R)-2-cyclopropyl-2-hydroxy-propyl)-6-(2-pyridin-2-yl-ethyl)-5-(4-trifluoromethyl-phenyl)-nicotinamide, and all pharmaceutically acceptable salts thereof.

Especially preferred is any compound selected from the group consisting of:

5-(4-chloro-phenyl)-6-(2-cyclopropyl-ethyl)-N-((1R,2R)-2-hydroxy-cyclohexyl)-nicotinamide, 5-(4-chloro-phenyl)-N-((1R,2R)-2-hydroxy-cyclohexyl)-6-(2-pyridin-3-yl-ethyl)-nicotinamide, 5-(4-chloro-phenyl)-N-((1R,2R)-2-hydroxy-cyclohexyl)-6-(2-pyridin-2-yl-ethyl)-nicotinamide, N-((1R,2R)-2-hydroxy-cyclohexyl)-6-(2-pyridin-3-yl-ethyl)-5-(4-trifluoromethyl-phenyl)-nicotinamide, N-((1R,2R)-2-hydroxy-cyclohexyl)-6-(2-pyridin-2-yl-ethyl)-5-(4-trifluoromethyl-phenyl)-nicotinamide, 5-(4-fluoro-phenyl)-N-((1R,2R)-2-hydroxy-cyclohexyl)-6-(2-thiazol-2-yl-ethyl)-nicotinamide, 5-(4-chloro-phenyl)-6-[2-(5-fluoro-pyridin-2-yl)-ethyl]-N-((1R,2R)-2-hydroxy-cyclohexyl)-nicotinamide and any pharmaceutically acceptable salt thereof.

The present invention also relates to a process for the manufacture of the compounds of formula I as defined above, which process comprises coupling a compound of formula

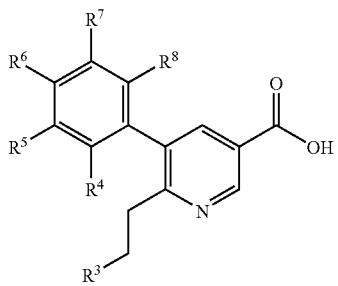

wherein $R^3$ to $R^8$ are as defined herein before, with an amine of the formula

H—NR$^1$R$^2$  III wherein $R^1$ and $R^2$ are as defined herein before, with the help of an coupling agent under basic conditions, and, if desired, converting the resulting compound of formula I into a pharmaceutically acceptable salt thereof.

Coupling agents for the reaction of compounds of formula II with amines of formula III are for example N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), or O-benzotriazol-1-yl-N,N,N',N'-tetramethyluronium tetrafluoroborate (TBTU). Preferred coupling agent is TBTU. Suitable bases include triethylamine, diisopropylethylamine and, preferably, Hünig's base.

Alternatively, the present invention relates to a process for the manufacture of the compounds of formula I as defined above, which process comprises hydrogenation of a compound of formula

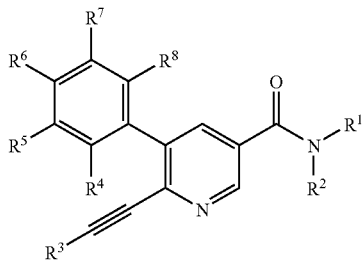

wherein $R^1$, $R^2$ and $R^3$ to $R^8$ are as defined herein before, in the presence of a catalyst, and, if desired, converting the resulting compound of formula I into a pharmaceutically acceptable salt thereof.

Preferably, the catalyst is palladium on charcoal.

Thus, the compounds of formula I can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

Compounds of formula I can be prepared according to scheme 1 starting from compound A by regioselective arylation using a suitable aryl metal species and catalyst system in an inert solvent to give an intermediate AB. Advantageously such a arylmetal species might be an arylboronic acid which is reacted with A in a inert solvent, for example toluene, in the presence of a palladium catalyst, for example tetrakis(triphenylphosphine)palladium(O) or bis(diphenylphoshinoferrocene)dichloropalladium(II), and a base, like sodium carbonate, at temperatures ranging from room temperature to the boiling point of the solvent.

Saponification of compounds of the formula AA to give compounds of the formula AB can be carried out in the presence of a suitable base such as a metal hydroxide, preferably lithium hydroxide, in an appropriate solvent such as tetrahydrofuran and mixtures thereof with water or methanol at temperatures ranging from 0° C. to 100° C., preferably at 20° C.

Coupling of compounds of the general formula AB with amines to give compounds of the general formula AC can be carried out by methods used for the formation of peptide bonds. In one particular aspect of the invention compounds of the general formula AC are activated with a coupling reagent, for example TBTU (O-benzotriazol-1-yloxy)-N,N,N',N'-tetramethyluronium tetrafluoroborate), and coupled to amines in an inert solvent such as DMF in the presence of suitable bases such as triethylamine or Huenig's base.

Compounds of the general formula AC can be transformed into compounds of the general formula AD by reaction with alkinyls of the general formula XB. Advantageously this reaction is run in the presence of a suitable catalyst system, for example bis(diphenylphoshinoferrocene)dichloropalladium (II), cuprous(I)iodide and triphenylphosphine on polystyrene in the presence of a suitable base, for example diisopropylethylamine or diethylamine, in a inert solvent, for example tetrahydrofuran or dimethylformamide in a microwave oven at 120° C.

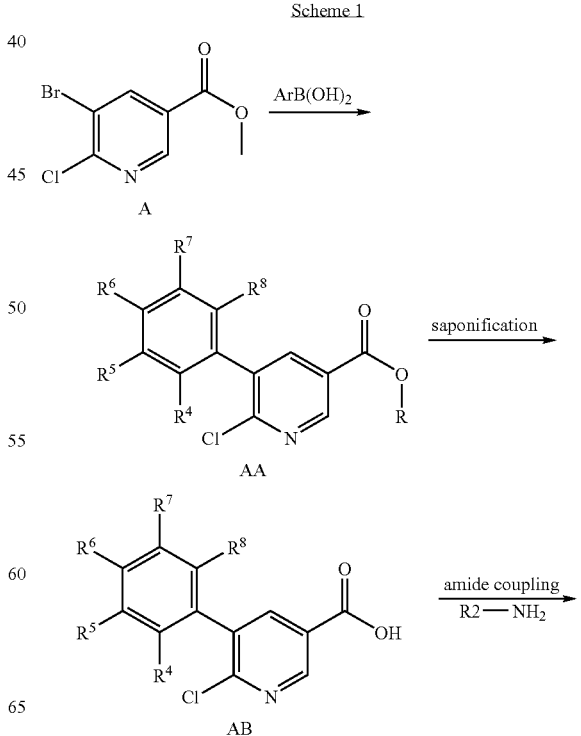

Scheme 1

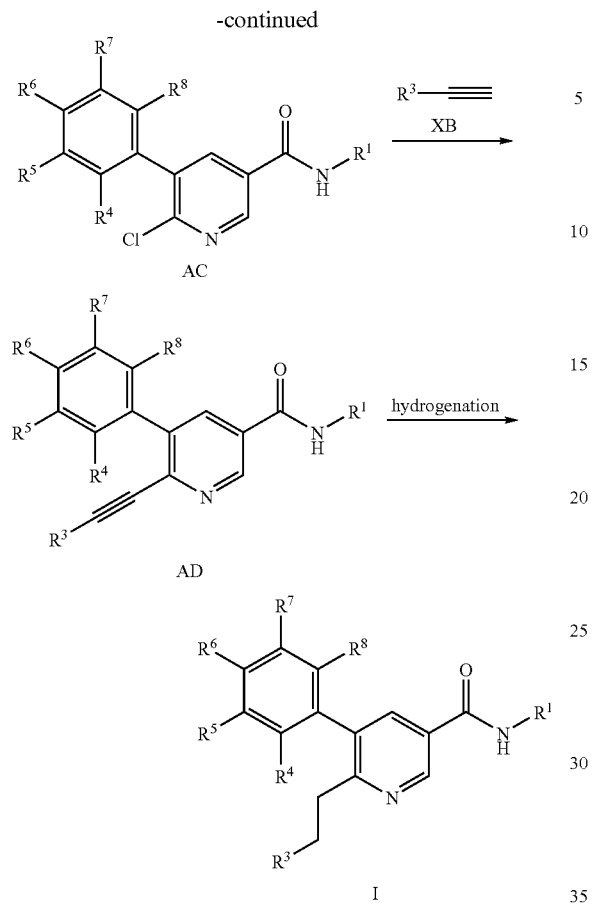

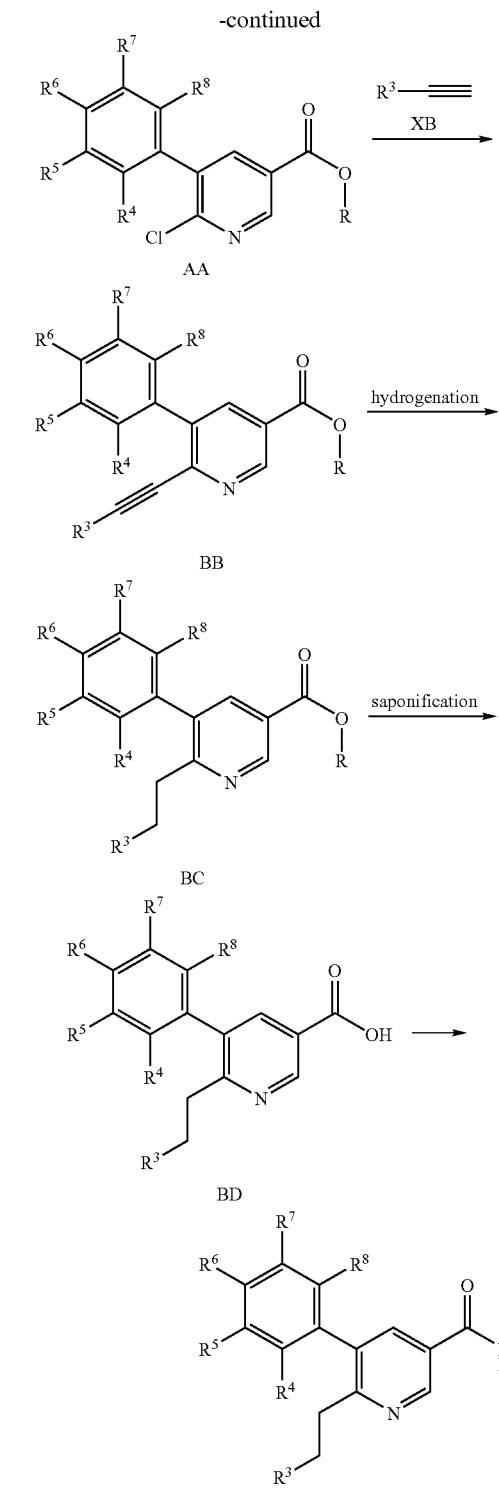

Compounds of the general formula AD can be hydrogenated to give compounds of formula I. Advantageously this reaction is run in the presence of a suitable catalyst system, for example palladium on charcoal, in a inert solvent for example ethyl acetate or ethanol, at suitable temperatures and pressures, for example at room temperature and hydrogen pressures of 1 bar.

Alternatively, compounds of the general formula AA can be transformed into compounds of the general formula BB by reaction with alkinyls of the general formula XB. Advantageously this reaction is run in the presence of a suitable catalyst system, for example bis(diphenylphoshinoferrocene) dichloropalladium(II), cuprous(I)iodide and triphenylphosphine on polystyrene in the presence of a suitable base, for example diisopropylethylamine or diethylamine, in a inert solvent, for example tetrahydrofuran or dimethylformamide in a microwave oven at 120° C.

Scheme 2

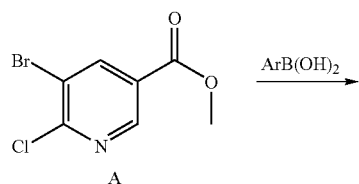

Compounds of the general formula BB can be hydrogenated to give compounds of formula BC. Advantageously this reaction is run in the presence of a suitable catalyst system, for example palladium on charcoal, in an inert solvent, for example ethyl acetate or ethanol, at suitable temperatures and pressures, for example at room temperature and hydrogen pressures of 1 bar.

Saponification of compounds of the formula BC to give compounds of the formula BD can be carried out in the presence of a suitable base such as a metal hydroxide, preferably lithium hydroxide, in an appropriate solvent such as tetrahydrofuran and mixtures thereof with water or methanol at temperatures ranging from 0° C. to 100° C., preferably at 20° C.

Coupling of compounds of the general formula BD with amines to give compounds of the general formula I can be carried out by methods used for the formation of peptide bonds. In one particular aspect of the invention compounds of the general formula BD are activated with a coupling reagent, for example TBTU (O-benzotriazol-1-yloxy)-N,N,N',N'-tetramethyluronium tetrafluoroborate), and coupled to amines in an inert solvent such as DMF in the presence of suitable bases such as triethylamine or Huenig's base.

Compounds of the general formula XB can, if $R^3$ represents an aryl or heteroaryl group, can be prepared according to Scheme 3.

An aryl or heteroaryl bromide of formula X is coupled in a Sonogashira type reaction with (trimethylsilyl)acetylene using a suitable catalyst system, for example tetrakis(triphenylphosphine)palladium(0) and cuprous(I)iodide, in an inert solvent, for example toluene, in the presence of a base, for example diisopropylamine, at elevated temperatures, for example 60° C., to give a compound of formula XA.

Deprotection of a compound of formula XA to obtain a compound of formula XB, can be achieved with a base, for example potassium carbonate, in a suitable solvent, for example methanol, at room temperature.

Scheme 3

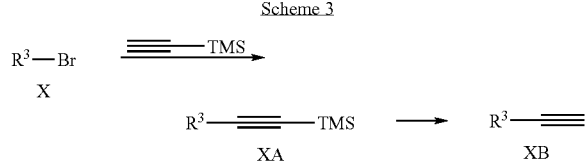

The invention further relates to compounds of formula I as defined above, when manufactured according to a process as defined above.

Some compounds of formula I may possess asymmetric centers and are therefore capable of existing in more than one stereoisomeric form. The invention thus also relates to compounds in substantially pure isomeric form at one or more asymmetric centers as well as mixtures, including racemic mixtures, thereof. Such isomers may be prepared by asymmetric synthesis, for example using chiral intermediates, or mixtures may be resolved by conventional methods, e.g., chromatography (chromatography with a chiral adsorbents or eluent), or use of a solving agent.

It will be appreciated, that the compounds of general formula I in this invention may be derivatized at functional groups to provide derivatives which are capable of conversion back to the parent compound in vivo.

As described above, the compounds of formula I or pharmaceutically acceptable salts thereof can be used as medicaments for the treatment and/or prophylaxis of diseases which are associated with the modulation of the CB1 receptors.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with the modulation of CB1 receptors.

In another embodiment, the invention relates to a method for the treatment and/or prophylaxis of diseases which are associated with the modulation of CB1 receptors, which method comprises administering a compound as defined above to a human being or animal.

The invention further relates to the use of compounds as defined above for the treatment and/or prophylaxis of diseases which are associated with the modulation of CB1 receptors.

In addition, the invention relates to the use of compounds as defined above for the preparation of medicaments or pharmaceutical compositions for the treatment and/or prophylaxis of diseases which are associated with the modulation of CB1 receptors. Such medicaments or compositions comprise a compound as defined above.

In this context, the expression 'diseases associated with modulation of CB1 receptors' means diseases which can be treated and/or prevented by modulation of CB1 receptors. Such diseases encompass, but are not limited to, psychic disorders, especially anxiety, psychosis, schizophrenia, depression, abuse of psychotropes, for example for the abuse and/or dependence of a substances, including alcohol dependency and nicotine dependency, neuropathies, multiple sclerosis, migraine, stress, epilepsy, dyskinesias, Parkinson's disease, amnesia, cognitive disorders, memory deficits, senile dementia, Alzheimer's disease, eating disorders, obesity, diabetes type II or non insulin dependent diabetes (NIDD), gastrointestinal diseases, vomiting, diarrhea, urinary disorders, cardiovascular disorders, infertility disorders, inflammations, infections, cancer, neuroinflammation, in particular in atherosclerosis, or the Guillain-Barrë syndrome, viral encephalitis, cerebral vascular incidents and cranial trauma.

In a preferable aspect, the expression 'diseases associated with modulation of CB1 receptors' relates to eating disorders, obesity, diabetes type II or non insulin dependent diabetes (NIDD), neuroinflammation, diarrhea, abuse and/or dependence of a substances, including alcohol dependency and nicotine dependency. In a more preferable aspect, the said term related to eating disorders, obesity, diabetes type II or non insulin dependent diabetes (NIDD), abuse and/or dependence of a substances, including alcohol dependency and nicotine dependency, with obesity being especially preferred.

It is a further preferred object to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include but are not limited to anorectic agents, lipase inhibitors and selective serotonin reuptake inhibitors (SSRI). Combinations or associations of the above agents may be encompassing separate, sequential or simultaneous administration.

Preferable lipase inhibitor is tetrahydrolipstatin.

Suitable anorectic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine, and pharmaceutically acceptable salts thereof.

Most preferable anorectic agents are sibutramine and phentermine.

Suitable selective serotonin reuptake inhibitors of use in combination with a compound of the present invention include: fluoxetine, fluvoxamine, paroxetine and sertraline, and pharmaceutically acceptable salts thereof.

It is a further preferred object to provide a method of treatment or prevention of Type II diabetes (non-insulin dependent diabetes mellitus (NIDDM) in a human which comprises administration of a therapeutically effective amount of a compound according to formula I in combination or association with a therapeutically effective amount of a lipase inhibitor, particularly, wherein the lipase inhibitor is orlistat. Also an object of the invention is the method as described above for the simultaneous, separate or sequential administration of a compound according to formula I and a lipase inhibitor, particularly tetrahydrolipstatin.

It is a further preferred object to provide a method of treatment or prevention of Type II diabetes (non-insulin dependent diabetes mellitus (NIDDM) in a human which comprises administration of a therapeutically effective amount of a compound according to formula I in combination or association with a therapeutically effective amount of an anti-diabetic agent selected from the group consisting of 1) PPARγ agonists such as pioglitazone or rosiglitazone, and the like; 2) biguanides such as metformin, and the like; 3) sulfonylureas such as glibenclamide, and the like; 4) PPARα/γ agonists such as GW-2331, and the like 5) DPP-IV-inhibitors such as LAF-237 (Vildagliptin) or MK-0431, and the like; 6) Glucokinase activators such as the compounds disclosed in e.g. WO 00/58293 A1, and the like. Also an object of the invention is the method as described above for the simultaneous, separate or sequential administration of a compound according to formula I and a therapeutically effective amount of an anti-diabetic agent as 1) PPARγ agonists such as pioglitazone or rosiglitazone, and the like; 2) biguanides such as metformin, and the like; 3) sulfonylureas such as glibenclamide, and the like; 4) PPARα/γ agonists such as GW-2331 GW-2331 and the like; 5) DPP-IV-inhibitors such as LAF-237 (Vildagliptin) or MK-0431, and the like; 6) Glucokinase activators such as the compounds disclosed in e.g. WO 00/58293 A1, and the like.

It is a further preferred object to provide a method of treatment or prevention of dyslipidemias in a human which comprises administration of a therapeutically effective amount of a compound according to formula I in combination or association with a therapeutically effective amount of a lipid lowering agent as 1) bile acid sequestrants such as cholestyramine, and the like; 2) HMG-CoA reductase inhibitors such as atorvastatin, and the like; 3) cholesterol absorption inhibitors such as ezetimibe, and the like; 4) CETP inhibitors such as torcetrapib, JTT 705, and the like; 5) PPARα-agonists such as beclofibrate, fenofibrate, and the like; 6) lipoprotein synthesis inhibitors such as niacin, and the like; and 7) niacin receptor agonists. Also an object of the invention is the method as described above for the simultaneous, separate or sequential administration of a compound according to formula I and a therapeutically effective amount of a lipid lowering agent as 1) bile acid sequestrants such as cholestyramine, and the like; 2) HMG-CoA reductase inhibitors such as atorvastatin, and the like; 3) cholesterol absorption inhibitors such as ezetimibe, and the like; 4) CETP inhibitors such as torcetrapib, JTT 705, and the like; 5) PPARα-agonists such as beclofibrate, fenofibrate, and the like; 6) lipoprotein synthesis inhibitors such as niacin, and the like; and 7) niacin receptor agonists.

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

In addition, to demonstrate CNS activities of the compounds of the present invention, the following in vivo assays may be used.

Method for Testing Task Learning and Spatial Memory

The Morris Water Maze is routinely used to assess task learning and spatial memory (Jaspers et al., Neurosci. Lett. 117:149-153, 1990; Morris, J. Neurosci. Methods 11:47-60, 1984). In this assay, animals are placed in a water pool which is divided into quadrants. One platform is hidden in one of the quadrants. The animal is placed in the water pool and is expected to locate the hidden platform within a predetermined time. During a number of training trials, the animal learns the location of the platform and escape from the pool. The animal receives multiple trials in this task. Total distance traveled, number of trials to locate platform, latency to find platform, and the swimming path is recorded for each animal. The animal's learning ability is measured by the length of time or number of trials required to find the hidden platform. Memory deficit or improvement is determined by the number of trials or the latency to find the platform at predetermined delay time after acquisition. Leaning and memory may be measured by the number of times that the animal crosses the quadrant where the platform was located during the acquisition phase.

Method for Testing Drug Dependence

Self-administration in animals is a predictor of a compound's abuse potential in humans. Modifications to this procedure may also be used to identify compounds that prevent or block the reinforcing properties of drugs that have abuse potential. A compound that extinguishes the self-administration of a drug may prevent that drug's abuse or its dependence. (Ranaldi et al., Psychopharmacol. 161:442-448, 2002; Campbell et al., Exp. Clin. Psychopharmacol. 8:312-25, 2000). In a self-administration test, animals are placed in the operant chambers containing both an active and inactive lever. Each response on the active lever produces an infusion of either the test compound or a drug known to be self-administered. Presses on the inactive lever have no effect, but are also recorded. Animals are then trained to self-administer compound/drug over a set period of time by having drug access during each daily session. Illumination of the chamber house light signals the beginning of the session and the availability of the compound/drug. When the session ends, the house light is turned off. Initially, a drug infusion occurs with every press of the active lever. Once lever-pressing behavior has been established, the number of presses to produce a drug infusion is increased. After stable compound/drug self-administration is obtained, the effect of a second compound on the drug-reinforced behavior may be evaluated. Administration of this second compound prior to the session can either potentiate, extinguish, or produce no change to the self-administrating behavior.

The following tests were carried out in order to determine the activity of the compounds of formula I.

The affinity of the compounds of the invention for cannabinoid CB1 receptors was determined using membrane preparations of human embryonic kidney (HEK) cells in which the human cannabis CB1 receptor is transiently transfected using the Semliki Forest Virus system in conjunction with [3H]-CP-55,940 as radioligand. After incubation of a freshly prepared cell membrane preparation with the [3H]-ligand, with or without addition of compounds of the invention, separation of bound and free ligand was performed by filtration over glass-fiber filters. Radioactivity on the filter was measured by liquid scintillation counting.

The affinity of the compounds of the invention for cannabinoid CB2 receptors was determined using membrane preparations of human embryonic kidney (HEK) cells in which the human cannabis CB2 receptor is transiently transfected using the Semliki Forest virus system in conjunction with [3H]-CP-55,940 as radioligand. After incubation of a freshly prepared cell membrane preparation with the [3H]-ligand, with or without addition of compounds of the invention, separation of bound of bound and free ligand was performed by filtration over glassfiber filters. Radioactivity on the filter was measured by liquid scintillation counting.

The cannabinoid CB1 antagonistic activity of compounds of the invention was determined by functional studies using CHO cells in which human cannabinoid CB1 receptors are stably expressed (see M. Rinaldi-Carmona et. al., J. Pharmacol. Exp. Ther. 278 (1996) 871). The stable expression of the human cannabinoid receptor in cell systems was first described in Nature 1990, 346, 561-564 (CB1) and Nature 1993, 365, 61-65 (CB2) respectively. Adenylyl cyclase was stimulated using forskolin and measured by quantifying the amount of accumulated cyclic AMP. Concomitant activation of CB1 receptors by CB1 receptor agonists (e.g. CP-55,940 or (R)-WIN-55212-2) can attenuate the forskolin-induced accumulation of cAMP in a concentration dependent manner. This CB 1 receptor mediated response can be antagonized by CB1 receptor antagonists such as the compounds of the invention.

The compounds of formula (I) show an excellent affinity for the CB1 receptor, determined with the experimental conditions described in Devane et al. Mol. Pharmacol. 34 (1988) 605-613. The compounds of the present invention or their pharmaceutically acceptable salts are antagonists and selective for the CB1 receptor with affinites below $K_i = 0.5$ μM, preferably below 200 nM, more preferably 1 nM to 100 nM. They exhibit at least a 10 fold selectivity against the CB2 receptor.

| Compound of Example | $K_i$ [μM] |
|---|---|
| 2 | 0.026 |
| 3 | 0.060 |
| 7 | 0.011 |

Effect of CB1 Receptor Antagonist/Inverse Agonist on CP 55,940-induced Hypothermia in NMRI ice Animals Male NMRI mice were used in this study and were obtained from Research Consulting Company Ltd (RCC) of Füllinsdorf (Switzerland). Mice, weighing 30-31 g were used in this study. Ambient temperature is approximately 20-21° C. and relative humidity 55-65%. A 12 hours light-dark cycle is maintained in the rooms with all tests being performed during the light phase. Access to tap water and food are ad libitum.

Method

All measurements were made between 12:00 am and 5:00 pm. Mice were brought in this environment and habituated for at least two hours before the start of the experiment. They had always free access to food and water. For each dose, 8 mice were used. Rectal body temperature measurements were recorded by mean of a rectal probe (RET2 of Physitemp) and digital thermometer (Digi-sense n°8528-20 of Cole Parmer, Chicago USA). The probe was inserted about 3.5 cm in each mouse.

The body temperature was taken 15 min before administration of either Vehicle or CB1 receptor antagonist/inverse agonist. 30 or 90 min after i.p. or p.o. administration of this compound, respectively, rectal body temperature was recorded in order to evaluate any influence of the compound itself. The CB receptor agonist CP 55,940 (0.3 mg/kg) was immediately administered intravenously, then 20 min after i.v. administration of CP 55940, body temperature was again measured.

The in vivo activity of compounds of formula (1) was assessed for their ability to regulate feeding behavior by recording food consumption in food deprived animals.

Rats were trained to have access to food for 2 h per day and were food deprived for 22 h. When they were trained under this schedule, the amount of food taken every day during these 2 h food intake session was consistent day after day.

To test the ability of compounds of formula I to decrease food intake, 8 animals were used in a cross-over study. Rats were individually housed in Plexiglas boxes with a grid on the floor and a paper was placed below the cage floor to collect any spillage. A food dispenser (becher) filled with a pre-weighed amount of food was presented to them for 2 h. At the end of the food intake session, rats returned to their home cage. Each rat was weighed before the start of the experiment and the amount of food consumed during this 2 h food intake session was recorded. Either various doses of test compound or vehicle was administered orally 60 min before the 2 h food intake session. A positive control Rimonabant (SR141716) was included in the experiment. An Anova analysis with repeated measures was used followed by a posthoc test Student Neumann-Keuls. *$P<0.05$ compared to Saline-treated rats.

Furthermore the utility of compounds of formula I in diseases or disorders may be demonstrated in animal disease models that have been reported in the literature. The following are examples of such animal disease models: a) reduction of sweet food intake in marmosets (Behavioral Pharm, 1998, 9, 179-181); b) reduction of sucrose and ethanol intake in mice (Psychopharm. 1997, 132, 104-106); c) increased motor activity and place conditioning in rats (Psychopharm. 1998, 135, 324-332; Psychopharmacol 2000, 151: 25-30); d) spontaneous locomotor activity in mice (J. Pharm. Exp. Ther. 1996, 277, 586-594); e) reduction in opiate self-administration in mice (Sci. 1999, 283, 401-404).

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatin capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatin capsules. Suitable carrier materials for soft gelatin capsules are, for example, vegetable oils, waxes, fats and semi-solid and liquid polyols (depending on the nature of the active ingredient no carriers might, however, be required in the case of soft gelatin capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following examples serve to illustrate the present invention in more detail. They are, however, not intended to limit its scope in any manner.

EXAMPLES

The following are a list of abbreviations and/or acronyms with their corresponding definitions used in the following examples:

LC=HPLC chromatography on an Atlantis C18 reverse phase column using a water/acetonitrile mobile phase (0.1% formic acid) linked to a Waters Micromass® ZQ™ mass spectrometer (Mobile phase: A=Formic acid (aq) 0.1%; B=Formic acid (acetonitrile) 0.1%; Flow rate 1 ml/min; Injection volume 3 mL; Detector 215 nm (nominal); Gradient Time/ % organic Phase: 0 min/5%, 2.5 min/100%, 2.7 min/100%, 2.71 min/5%, 3.0 min/5%); Rt=retention time. MS=mass spectrometry; EI=electron impact; ISP=ion spray, (M+H)=the molecular weight of the compound plus a proton, and ES=electrospray. NMR data are reported in parts per million (δ) relative to internal tetramethylsilane and are referenced to the deuterium lock signal from the sample solvent ($d_6$-DMSO unless otherwise stated); coupling constants (J) are in Hertz. mp=melting point; bp=boiling point; TBTU=O-(Benzotriazol-1-yl)-N,N,N',N'-tetramethyl-uronium-tetrafluoroborate; DMF=dimethylformamide, dppf=1,1'-bis(diphenylphosphino)ferrocene; PyBOP=Benzotriazol-1-yloxy)tripyrrolidino-phosphonium hexafluorophosphate.

Example 1

5-(4-Chloro-phenyl)-N-((1R,2R)-2-hydroxy-cyclohexyl)-6-(3-methoxy-propyl)-nicotinamide a) 6-Chloro-5-(4-chloro-phenyl)-nicotinic acid methyl ester To a solution of 5-bromo-6-chloro-nicotinic acid methyl ester (10 g, 40 mmol) in toluene (200 mL) was added 4-chlorophenyl-boronic acid (6.4 g, 40 mmol), [1,1'-bis(diphenylphosphino)ferrrocene]dichlorpalladium(II) dichloromethane complex (1.6 g, 2 mmol) and 2 M sodiumcarbonate solution (60 mL). The reaction mixture was stirred for 2 h at 90° C. After cooling, the phases were separated; the aqueous phase was extracted once with ethyl acetate (200 mL), organic phases were washed once with water and brine (150 mL each), combined and dried over $MgSO_4$. After evaporation of the solvent the crude product was purified by flash column chromatography (dichloromethane/heptane 2:1 to 9:1) to give 6-chloro-5-(4-chlorophenyl)-nicotinic acid methyl ester as a colorless solid, 8.12 g (72% yield). m/z ($ES^+$): 281.1, 283.1 (M+H).

b) 6-Chloro-5-(4-chloro-phenyl)-nicotinic acid

Lithiumhydroxide monohydrate (2.41 g, 57 mmol) was added to a solution of 6-chloro-5-(4-chloro-phenyl)-nicotinic acid methyl ester (8.1 g, 29 mmol) in tetrahydrofuran (120 mL) and water (34 mL) under nitrogen at room temperature. The reaction mixture was stirred for 20 h at room temperature, poured onto ice/water (200 g), acidified with 1 N HCl (120 mL) and the whole was extracted with ethyl acetate (250 mL). The water phase was extracted twice with ethylacetate (2×200 mL), organic phases were combined, dried over MgSO4 and concentrated in vacuo. 6-chloro-5-(4-chlorophenyl)-nicotinic acid was isolated as a colorless solid and used without further purification; 7.30 g (94% yield). m/z (ISP$^-$): 266.1 (M−H).

c) 6-Chloro-5-(4-chloro-phenyl)-N-((1R,2R)-2-hydroxy-cyclohexyl)-nicotinamide 6-Chloro-5-(4-chloro-phenyl)-nicotinic acid (1.4 g, 5 mmol) was dissolved in N,N-dimethylformamide (30 mL). To this solution was added sequentially (1R,2R)-2-aminocyclohexanol hydrochloride (0.87 g, 6 mmol), TBTU (1.84 g, 6 mmol), and N-ethyldiisopropylamine (4.47 mL, 26 mmol). The reaction mixture was stirred at room temperature for 72 hours then concentrated in vacuo. The residue was then dissolved in ethyl acetate (100 mL) and washed with 0.5 N HCl (100 mL), saturated sodium bicarbonate (100 mL) and water (100 mL). The aqueous phases were extracted with ethyl acetate (2×100 mL), the organics were combined and the whole was dried over MgSO4 and concentrated in vacuo. The solid residue was purified by stirring with (ethylacetate/heptane 1:2, 50 mL) to give 6-chloro-5-(4-chloro-phenyl)-N-((1R,2R)-2-hydroxy-cyclohexyl)-nicotinamide as a colorless solid, 1.4 g (73% yield). m/z (ISP$^+$): 364.9, 366.9 (M+H).

d) 5-(4-Chloro-phenyl)-N-((1R,2R)-2-hydroxy-cyclohexyl)-6-(3-methoxy-prop-1-ynyl)-nicotinamide Bis(triphenylphosphine)palladium (II) dichloride (52 mg, 0.074 mmol), cuprous (I) iodide (14 mg, 0.074 mmol), triphenylphosphine polystyrene resin(146 mg, 1.48 mmol/g) and propargyl methylether (104 mg, 1.48 mmol) were added under argon at room temperature to a solution of 6-chloro-5-(4-chloro-phenyl)-N-((1R,2R)-2-hydroxy-cyclohexyl)-nicotinamide (450 mg, 1.23 mmol) in N,N-dimethylformamide. The mixture was irradiated for 70 min in a microwave oven at 120° C. The polystyrene resin was filtered off and washed with ethylacetate. The filtrate was treated with 1 N HCl (80 mL); phases were separated and the water phase was extracted with ethyl acetate (2×100 mL). The organic phases were washed with water (100 mL) and saturated sodium bicarbonate solution (100 mL). Organic phases were then combined, dried over MgSO4 and concentrated in vacuo. The residue was purified by flash column chromatography (heptane/ethyl acetate 1:2 to 1:9) to give 5-(4-chloro-phenyl)-N-((1R,2R)-2-hydroxy-cyclohexyl)-6-(3-methoxy-prop-1-ynyl)-nicotinamide as a light yellow solid; 0.13 g (26% yield). m/z (ISP$^+$): 399.1 (M+H).

e) 5-(4-Chloro-phenyl)-N-((1R,2R)-2-hydroxy-cyclohexyl)-6-(3-methoxy-propyl)-nicotinamide Palladium on charcoal (18 mg, 10%) was added to a solution of 5-(4-chloro-phenyl)-N-((1R,2R)-2-hydroxy-cyclohexyl)-6-(3-methoxy-prop-1-ynyl)-nicotinamide (100 mg, 0.25 mmol) in ethylacetate (12 mL). The mixture was hydrogenated for 2 h at room temperature and 0.4 bar positive hydrogen pressure after which the theoretical amount of hydrogen had been consumed. The catalyst was then filtered off and the solvent was evaporated to afford 5-(4-Chlorophenyl)-N-((1R,2R)-2-hydroxy-cyclohexyl)-6-(3-methoxypropyl)-nicotinamide without further purification as a orange solid 93 mg (92% yield). m/z (ISP$^+$): 403.2, 405.2 (M+H).

Example 2

5-(4-Chloro-phenyl)-6-(2-cyclopropyl-ethyl)-N-((1R,2R)-2-hydroxy-cyclohexyl)-nicotinamide The title compound was synthesized in analogy to Examples 1d to 1e, using 6-chloro-5-(4-chloro-phenyl)-N-((1R,2R)-2-hydroxy-cyclohexyl)-nicotinamide and ethynylcyclopropane as starting materials; yield 189 mg, 46% over two steps; m/z (ISP$^+$): 399.2, 401.3 (M+H).

Example 3

N-((1R,2R)-2-Hydroxy-cyclohexyl)-6-(2-pyrimidin-5-yl-ethyl)-5-(4-trifluoromethyl-phenyl)-nicotinamide a) 5-Trimethylsilanylethynyl-pyrimidine

Tetrakis(triphenylphosphine)palladium(O) (727 mg, 0.6 mmol) was added to a stirred, degassed suspension of 5-bromopyrimidine (5.0 g, 31.4 mmol) and copper(I)iodide (120 mg, 0.6 mmol) in toluene and diisopropylamine (1:1, 200 ml) under nitrogen. The reaction mixture was heated to 60° C., trimethylsilylacetylene (4.89 ml, 34.6 mmol) was added and the reaction mixture was stirred for 3 hours at 60° C. The reaction mixture was allowed to cool to room temperature, diluted with ethyl acetate (200 ml) and washed with saturated aqueous ammonium chloride solution (3×100 ml). The organic layer was separated, dried over MgSO4 and concentrated in vacuo. The crude product was purified by flash column chromatography (5% ethyl acetate/heptane) to give 5-trimethylsilanylethynyl-pyrimidine as a pale brown solid, 4.71 g (85% yield). LC at 215 nm; Rt 2.07: 88%, m/z (ES$^+$): 177 (M+H).

b) 5-Ethynyl-pyrimidine

Potassium carbonate (7.38 g, 53.4 mmol) was added in one portion to a stirred solution of 5-trimethylsilanylethynyl-pyrimidine (4.71 g, 26.7 mmol) in methanol (10 ml). The reaction mixture was stirred for 2 hours at room temperature then concentrated in vacuo. The residue was suspended in dichloromethane and the inorganic solids were removed by filtration. The filtrate was concentrated in vacuo to remove ca. 95% of the solvent to afford 5-ethynyl-pyrimidine as a brown oil in crude form. This material was used in the subsequent Sonogashira reaction without further purification.

c) 6-Chloro-5-(4-trifluoromethyl-phenyl)-nicotinic acid ethyl ester and 6-chloro-5-(4-trifluoromethyl-phenyl)-nicotinic acid methyl ester Tetrakis(triphenylphosphine)palladium(0) (104 mg, 0.9 mmol) was added to a degassed suspension of 5-bromo-6-chloro-nicotinic acid methyl ester (4.50 g, 18.0 mmol), 4-(trifluoromethyl)-phenylboronic acid (3.76 g, 19.8 mmol) and potassium carbonate (4.98 g, 36 mmol) in toluene and ethanol (2:1, 50 ml). The reaction mixture was stirred at 80° C. for 16 hours then cooled to room temperature, water (50 ml) was added and the whole was extracted with ethyl acetate (3×100 ml). The organics were combined, dried over MgSO4 and concentrated in vacuo. The residue was purified by flash column chromatography (20% ethyl acetate/heptane) to afford a mixture of 6-chloro-5-(4-trifluoromethyl-phenyl)-nicotinic acid ethyl ester and 6-chloro-5-(4-trifluoromethylphenyl)-nicotinic acid methyl ester in a 45:55 ratio, 2.46 g (42% yield). LC at 215 nm; Rt 2.31: 53%, m/z (ES$^+$): 316 (M+H) and Rt 2.43: 44%, m/z (ES$^+$): 330 (M+H).

d) 6-Pyrimidin-5-yl-ethynyl-5-(4-trifluoromethyl-phenyl)-nicotinic acid ethyl ester and 6-pyrimidin-5-ylethynyl-5-(4-trifluoromethyl-phenyl)-nicotinic acid methyl ester A degassed solution of 5-ethynyl-pyrimidine (2.0 mmol) in tetrahydrofuran and N-ethyldiisopropylamine (1:1, 10 ml) was added to a degassed suspension of 2-chloro-5-(4-trifluoromethyl-phenyl)-nicotinic acid ethyl ester and 2-chloro-5-(4-trifluoromethyl-phenyl)-nicotinic acid methyl ester (45:55, 296 mg, 1.0 mmol), [1,1'-bis(diphenylphosphino)ferrocene]palladium(II) dichloride dichloromethane complex (1:1) (49 mg, 0.06 mmol), polymer supported triphenylphoshine (135 mg, 1.48 mmol/g, 0.2 mmol) and copper (I)iodide (11 mg, 0.06 mmol) in tetrahydrofuran and N-ethyldiisopropylamine (1:1, 5 ml). The reaction mixture was heated at 120° C. for 20 hours under an atmosphere of nitrogen. The reaction mixture was cooled to room temperature and the solids were removed by filtration. The solids were washed with ethyl acetate (100 ml), the organic liquors were combined and washed with saturated aqueous ammonium chloride solution (3×50 ml). The organic layer was then dried over MgSO4 and concentrated in vacuo. Purification by flash column chromatography (20% ethyl acetate/heptane) gave a mixture of 6-pyrimidin-5-ylethynyl-5-(4-trifluoromethyl-phenyl)-nicotinic acid ethyl ester and 6-pyrimidin-5-ylethynyl-5-(4-trifluoromethyl-phenyl)-nicotinic acid methyl ester as a brown oil in a 1:1 ratio, 330 mg (83% yield). LC at 215 nm; Rt 2.21: 43%, m/z (ES$^+$): 384 (M+H) and Rt 2.33: 43%, m/z (ES$^+$): 398 (M+H).

e) 6-(2-Pyrimidin-5-yl-ethyl)-5-(4-trifluoromethyl-phenyl)-nicotinic acid ethyl ester and 6-(2-pyrimidin-5-yl-ethyl)-5-(4-trifluoromethyl-phenyl)-nicotinic acid methyl ester Palladium on carbon (10% w/w, 30 mg) was added to a solution of 6-pyrimidin-5-ylethynyl-5-(4-trifluoromethyl-phenyl)-nicotinic acid ethyl ester and 6-pyrimidin-5-ylethynyl-5-(4-trifluoromethyl-phenyl)-nicotinic acid methyl ester (1:1, 330 mg, 0.83 mmol) in ethanol (10 ml). The reaction mixture was stirred at room temperature under an atmosphere of hydrogen for 20 hours. The reaction vessel was purged with nitrogen and catalyst was removed by filtration. The reaction mixture was concentrated in vacuo to give a mixture of 6-(2-pyrimidin-5-yl-ethyl)-5-(4-trifluoromethyl-phenyl)-nicotinic acid ethyl ester and 6-(2-pyrimidin-5-yl-ethyl)-5-(4-trifluoromethyl-phenyl)-nicotinic acid methyl ester in a 46:54 ratio, 196 mg (59% yield). LC at 215 nm; Rt 2.05: 47%, m/z (ES$^+$): 388 (M+H) and Rt 2.18: 40%, m/z (ES$^+$): 402 (M+H).

f) 6-(2-Pyrimidin-5-yl-ethyl)-5-(4-trifluoromethyl-phenyl)-nicotinic acid

Aqueous 1M lithium hydroxide solution (2.25 ml, 2.25 mmol) was added to a solution of 6-(2-pyrimidin-5-yl-ethyl)-5-(4-trifluoromethyl-phenyl)-nicotinic acid ethyl ester and 6-(2-pyrimidin-5-yl-ethyl)-5-(4-trifluoromethyl-phenyl)-nicotinic acid methyl ester (46:54, 196 mg, 0.49 mmol) in tetrahydrofuran and methanol (6:1, 7 ml). The reaction mixture was stirred for 20 hours at room temperature then concentrated in vacuo. The residue was treated with 4M HCl in dioxane (0.56 ml, 2.25 mmol) and concentrated in vacuo to give crude 6-(2-pyrimidin-5-yl-ethyl)-5-(4-trifluoromethyl-phenyl)-nicotinic acid. This material was used in the subsequent amide coupling step without further purification. LC at 215 nm; Rt 1.72: 89%, m/z (ES$^+$): 374 (M+H).

g) N-((1R,2R)-2-Hydroxy-cyclohexyl)-6-(2-pyrimidin-5-yl-ethyl)-5-(4-trifluoromethyl-phenyl)-nicotinamide A solution of (1R,2R)-2-amino-cyclohexanol hydrochloride (41 mg, 0.27 mmol) in N,N-dimethylformamide (1.2 ml) was added to a suspension of TBTU (234 mg, 0.73 mmol), 6-(2-pyrimidin-5-yl-ethyl)-5-(4-trifluoromethyl-phenyl)-nicotinic acid (0.24 mmol) and N-ethyldiisopropylamine (0.21 ml, 1.22 mmol) in N,N-dimethylformamide (1.7 ml). The reaction mixture was shaken at room temperature for 20 hours then concentrated in vacuo. The residue was then dissolved in dichloromethane (2 ml) and washed with water (2 ml). The aqueous layer was separated and extracted with dichloromethane (2 ml), the organics were combined and the whole was dried over MgSO4 and concentrated in vacuo. The residue was purified by preparative HPLC to afford N-((1R,2R)-2-hydroxy-cyclohexyl)-6-(2-pyrimidin-5-yl-ethyl)-5-(4-trifluoromethyl-phenyl)-nicotinamide, 49 mg (44% yield over 2 steps). LC at 215 nm; Rt 3.92: 92%, m/z (ES$^+$): 471 (M+H).

Example 4

5-(4-Chloro-phenyl)-N—((R)-2-cyclopropyl-2-hydroxy-propyl)-6-(2-pyridin-3-yl-ethyl)-nicotinamide The title compound was synthesized in analogy to Example 3, using 3-bromopyridine, 5-bromo-6-chloro-nicotinic acid methyl ester, 4-chloro-phenylboronic acid and (R)-1-amino-2-cyclopropyl-propan-2-ol as starting materials; yield over the last 2 steps 5.9 mg, 5% over 2 steps. LC at 215 nm; Rt 3.17: 93%, m/z (ES$^+$): 436 (M+H).

Example 5

5-(4-Fluoro-phenyl)-N-((1R,2R)-2-hydroxy-cyclohexyl)-6-(2-pyridin-3-yl-ethyl)-nicotinamide The title compound was synthesized in analogy to Example 3, using 3-bromopyridine, 5-bromo-6-chloro-nicotinic acid methyl ester, 4-fluoro-phenylboronic acid and (1R,2R)-2-amino-cyclohexanol as starting materials; yield over the last 2 steps 11.0 mg, 7%. LC at 215 nm; Rt 2.95: 98%, m/z (ES$^+$): 420 (M+H).

Example 6

5-(4-Fluoro-phenyl)-6-[2-(5-fluoro-pyridin-2-yl)-ethyl]-N-((1R,2R)-2-hydroxy-cyclohexyl)-nicotinamide The title compound was synthesized in analogy to Example 3, using 2-bromo-5-fluoropyridine, 5-bromo-6-chloro-nicotinic acid methyl ester, 4-fluoro-phenylboronic acid and (1R,2R)-2-amino-cyclohexanol as starting materials; yield over the last 2 steps 31.7 mg, 27%. LC at 215 nm; Rt 3.88: 100%, m/z (ES$^+$): 438 (M+H).

Example 7

5-(4-Chloro-phenyl)-N-((1R,2R)-2-hydroxy-cyclohexyl)-6-(2-pyridin-3-yl-ethyl)-nicotinamide The title compound was synthesized in analogy to Example 3, using 3-bromopyridine, 5-bromo-6-chloro-nicotinic acid methyl ester, 4-chloro-phenylboronic acid and (1R,2R)-2-amino-cyclohexanol as starting materials; yield over the last 2 steps 24.7 mg, 19%. LC at 215 nm; Rt 3.12: 99%, m/z (ES$^+$): 436 (M+H).

Example 8

5-(4-Chloro-phenyl)-N-((1R,2R)-2-hydroxy-cyclohexyl)-6-(2-pyridin-2-yl-ethyl)-nicotinamide The title compound was synthesized in analogy to Example 3, using 2-bromopyridine, 5-bromo-6-chloro-nicotinic acid methyl ester, 4-chloro-phenylboronic acid and (1R,2R)-2-amino-cyclohexanol as starting materials; yield over the last 2 steps 28.0 mg, 21%. LC at 215 nm; Rt 3.10: 98%, m/z (ES$^+$): 436 (M+H).

Example 9

N-((1R,2R)-2-Hydroxy-cyclohexyl)-6-(2-pyridin-3-yl-ethyl)-5-(4-trifluoromethyl-phenyl)-nicotinamide The title compound was synthesized in analogy to Example 3, using 3-bromopyridine, 5-bromo-6-chloro-nicotinic acid methyl ester, 4-trifluoromethyl-phenylboronic acid and (1R,2R)-2-amino-cyclohexanol as starting materials; yield over the last 2 steps 7.2 mg, 19%. LC at 215 nm; Rt 3.28: 94%, m/z (ES$^+$): 470 (M+H).

Example 10

N-((1R,2R)-2-Hydroxy-cyclohexyl)-6-(2-pyridin-2-yl-ethyl)-5-(4-trifluoromethyl-phenyl)-nicotinamide The title compound was synthesized in analogy to Example 3, using 2-bromopyridine, 5-bromo-6-chloro-nicotinic acid methyl ester, 4-trifluoromethyl-phenylboronic acid and (1R,2R)-2-amino-cyclohexanol as starting materials; yield over the last 2 steps 35.2 mg, 22%. LC at 215 nm; Rt 3.25: 93%, m/z (ES$^+$): 470 (M+H).

Example 11

5-(4-Fluoro-phenyl)-N-((1R,2R)-2-hydroxy-cyclohexyl)-6-(2-pyridin-2-yl-ethyl)-nicotinamide The title compound was synthesized in analogy to Example 3, using 2-bromopyridine, 5-bromo-6-chloro-nicotinic acid methyl ester, 4-fluoro-phenylboronic acid and (1R,2R)-2-amino-cyclohexanol as starting materials; yield over the last 2 steps 10.0 mg, 10%. LC at 215 nm; Rt 2.95: 94%, m/z (ES$^+$): 420 (M+H).

Example 12

5-(4-Fluoro-phenyl)-N-((1R,2R)-2-hydroxy-cyclohexyl)-6-(2-pyridin-4-yl-ethyl)-nicotinamide The title compound was synthesized in analogy to Example 3, using 4-bromopyridine, 5-bromo-6-chloro-nicotinic acid methyl ester, 4-fluoro-phenylboronic acid and (1R,2R)-2-amino-cyclohexanol as starting materials; yield over the last 2 steps 9.0 mg, 24%. LC at 215 nm; Rt 2.93: 86%, m/z (ES$^+$): 420 (M+H).

Example 13

5-(4-Fluoro-phenyl)-N-((1R,2R)-2-hydroxy-cyclohexyl)-6-(2-thiazol-2-yl-ethyl)-nicotinamide The title compound was synthesized in analogy to Example 3, using 2-bromothiazole, 5-bromo-6-chloro-nicotinic acid methyl ester, 4-fluoro-phenylboronic acid and (1R,2R)-2-amino-cyclohexanol as starting materials; yield over the last 2 steps 14.7 mg, 11%. LC at 215 nm; Rt 3.85: 93%, m/z (ES$^+$): 426 (M+H).

Example 14

5-(4-Chloro-phenyl)-N-((1R,2R)-2-hydroxy-cyclohexyl)-6-(2-pyrimidin-5-yl-ethyl)-nicotinamide The title compound was synthesized in analogy to Example 3, using 5-bromopyrimidine, 5-bromo-6-chloro-nicotinic acid methyl ester, 4-chloro-phenylboronic acid and (1R,2R)-2-amino-cyclohexanol as starting materials; yield over the last 2 steps 44.4 mg, 34%. LC at 215 nm; Rt 3.78: 94%, m/z (ES$^+$): 437 (M+H).

Example 15

5-(4-Chloro-phenyl)-6-[2-(5-fluoro-pyridin-2-yl)-ethyl]-N-((1R,2I)-2-hydroxy-cyclohexyl)-nicotinamide The title compound was synthesized in analogy to Example 3, using 2-bromo-5-fluoro-pyridine, 5-bromo-6-chloro-nicotinic acid methyl ester, 4-chloro-phenylboronic acid and (1R,2R)-2-amino-cyclohexanol as starting materials; yield over the last 2 steps 21.4 mg, 43%. LC at 215 nm; Rt 4.12: 99%, m/z (ES$^+$): 454 (M+H).

Example 16

6-[2-(5-Fluoro-pyridin-2-yl)-ethyl]-N-((1R,2R)-2-hydroxy-cyclohexyl)-5-(4-trifluoromethyl-phenyl)-nicotinamide The title compound was synthesized in analogy to Example 3, using 2-bromo-5-fluoro-pyridine, 5-bromo-6-chloro-nicotinic acid methyl ester, 4-trifluoromethyl-phenyl-boronic acid and (1R,2R)-2-amino-cyclohexanol as starting materials; yield over the last 2 steps 14.5 mg, 33%. LC at 215 nm; Rt 4.26: 95%, m/z (ES$^+$): 488 (M+H).

Example 17

N—((R)-2-Cyclopropyl-2-hydroxy-propyl)-5-(4-fluoro-phenyl)-6-(2-pyridin-4-yl-ethyl)-nicotinamide The title compound was synthesized in analogy to Example 3, using 4-bromo-pyridine, 5-bromo-6-chloro-nicotinic acid methyl ester, 4-trifluoromethyl-phenylboronic acid and (R)-1-amino-2-cyclopropyl-propan-2-ol as starting materials; yield over the last 2 steps 14.2 mg, 38%. LC at 215 nm; Rt 2.93: 95%, m/z (ES$^+$): 420 (M+H).

Example 18

N—((R)-2-Cyclopropyl-2-hydroxy-propyl)-5-(4-fluoro-phenyl)-6-(2-thiazol-2-yl-ethyl)-nicotinamide The title compound was synthesized in analogy to Example 3, using 2-bromo-thiazole, 5-bromo-6-chloro-nicotinic acid methyl ester, 4-fluoro-phenylboronic acid and (R)-1-amino-2-cyclopropyl-propan-2-ol as starting materials; yield over the last 2 steps 14.2 mg, 11%. LC at 215 nm; Rt 3.91: 97%, m/z (ES$^+$): 426 (M+H).

Example 19

5-(4-Chloro-phenyl)-N—((R)-2-cyclopropyl-2-hydroxy-propyl)-6-(2-pyridin-2-yl-ethyl)-nicotinamide The title compound was synthesized in analogy to Example 3, using 2-bromo-pyridine, 5-bromo-6-chloro-nicotinic acid methyl ester, 4-chloro-phenylboronic acid and (R)-1-amino-2-cyclopropyl-propan-2-ol as starting materials; yield over the last 2 steps 17.0 mg, 13%. LC at 215 nm; Rt 3.16: 88%, m/z (ES+): 436 (M+H).

Example 20

N—((R)-2-Cyclopropyl-2-hydroxy-propyl)-6-(2-pyridin-2-yl-ethyl)-5-(4-trifluoromethyl-phenyl)-nicotinamide The title compound was synthesized in analogy to Example 3, using 2-bromo-pyridine, 5-bromo-6-chloro-nicotinic acid methyl ester, 4-trifluoromethyl-phenylboronic acid and (R)-1-amino-2-cyclopropyl-propan-2-ol as starting materials; yield over the last 2 steps 22.4 mg, 14%. LC at 215 nm; Rt 3.31: 98%, m/z (ES+): 470 (M+H).

Galenical Examples

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

Unless stated to the contrary, all compounds in the examples were prepared and characterized as described. All ranges recited herein encompass all combinations and sub-combinations included within that range limit. All patents and publications cited herein are hereby incorporated by reference in their entirety.

The invention claimed is:

1. A compound of the formula:

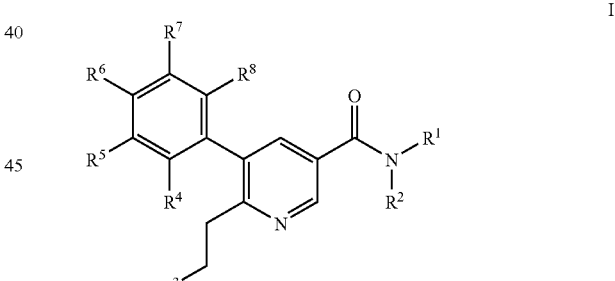

I or a pharmaceutically acceptable salt thereof,
wherein:
(a) $R^1$ is selected from the group consisting of:
  (1) cycloalkyl which is optionally substituted by hydroxy or lower alkoxy,
  (2) lower hydroxyalkyl,
  (3) lower hydroxyhalogenalkyl,
  (4) —$CH_2$—$CR^9R^{10}$-cycloalkyl, wherein (i) $R^9$ is hydrogen or lower alkyl and (ii) $R^{10}$ is hydrogen, hydroxy or lower alkoxy; and
  (5) —$CR^{11}R^{12}$—$COOR^{13}$; wherein (i) $R^{10}$ is hydrogen, hydroxy or lower alkoxy, (ii) $R^{11}$ and $R^{12}$ independently from each other are hydrogen or lower alkyl; and (iii) $R^{13}$ is lower alkyl;
(b) $R^2$ is hydrogen;
(c) $R^3$ is selected from the group consisting of:

(1) cycloalkyl,
(2) lower cycloalkylalkyl,
(3) lower alkoxy,
(4) lower alkoxyalkyl,
(5) halogen,
(6) lower halogenalkyl,
(7) phenyl, which is unsubstituted or mono-substituted or di-substituted independently by lower alkyl or halogen,
(8) lower phenylalkyl, wherein said phenyl is unsubstituted or mono-substituted or di-substituted independently by lower alkyl or halogen,
(9) heteroaryl, which is unsubstituted or mono-substituted or di-substituted independently by lower alkyl or halogen, and
(10) lower heteroarylalkyl, wherein the heteroaryl group is unsubstituted or mono-substituted or di-substituted independently by lower alkyl or halogen;
(d) $R^4$ and $R^8$ independently from each other are hydrogen or halogen;
(e) $R^5$ and $R^7$ independently from each other are selected from the group consisting of hydrogen, halogen, lower halogenalkyl, lower halogenoalkoxy, and cyano; and
(f) $R^6$ is selected from the group consisting of hydrogen, halogen, lower halogenalkyl, lower halogenalkoxy, and cyano.

2. A compound according to claim 1, wherein $R^1$ is selected from the group consisting of:
(1) cycloalkyl, which is optionally substituted by hydroxy or lower alkoxy, and
(2) —$CH_2$—$CR^9R^{10}$-cycloalkyl, wherein (i) $R^9$ is hydrogen or lower alkyl and (ii) $R^{10}$ is selected from hydrogen, hydroxy and lower alkoxy.

3. A compound according to claim 1, wherein $R^1$ is cycloalkyl substituted by hydroxy.

4. A compound according to claim 1, wherein $R^1$ is —$CH_2$—$CR^9R^{10}$-cycloalkyl and wherein: (i) $R^9$ is hydrogen or lower alkyl and (ii) $R^{10}$ is hydrogen, hydroxy, and lower alkoxy.

5. A compound according to claim 1, wherein $R^1$ is —$CH_2$—$CR^9R^{10}$-cycloalkyl and wherein $R^9$ is methyl and $R^{10}$ is hydroxy.

6. A compound according to claim 1, wherein $R^3$ is selected from the group consisting of:
(1) cycloalkyl,
(2) lower cycloalkylalkyl,
(3) lower alkoxy,
(4) lower alkoxyalkyl,
(5) heteroaryl, which is unsubstituted or mono-substituted or di-substituted independently by lower alkyl or halogen, and
(6) lower heteroarylalkyl, wherein the heteroaryl group is unsubstituted or mono-substituted or di-substituted independently by lower alkyl or halogen.

7. A compound according to claim 1, wherein $R^3$ is selected from the group consisting of cycloalkyl, lower alkoxyalkyl, and heteroaryl which is unsubstituted or mono-substituted or di-substituted independently by lower alkyl or halogen.

8. A compound according claim 1, wherein $R^3$ is cycloalkyl.

9. A compound according to claim 1, wherein $R^3$ is lower alkoxyalkyl.

10. A compound according to claim 1, wherein $R^3$ is heteroaryl which is unsubstituted or mono-substituted or di-substituted independently by lower alkyl or halogen.

11. A compound according to claim 1, wherein $R^3$ is heteroaryl selected from the group consisting of pyridyl, pyrimidinyl and thiazolyl, wherein said heteroaryl is unsubstituted or mono-substituted or di-substituted independently by lower alkyl or halogen.

12. A compound according to claim 1, wherein: (a) $R^4$ and $R^8$ independently from each other are hydrogen or halogen, (b) $R^5$ and $R^7$ independently from each other are selected from the group consisting of hydrogen, halogen, lower halogenalkyl, lower halogenalkoxy and cyano, (c) $R^6$ is selected from the group consisting of hydrogen, halogen, lower halogenalkyl, lower halogenalkoxy and cyano, and (d) not all of $R^4$ to $R^8$ are hydrogen.

13. A compound according to claim 1, wherein $R^6$ is halogen or lower halogenalkyl and $R^4$, $R^5$, $R^7$ and $R^8$ are hydrogen.

14. A compound according to claim 1, wherein $R^6$ is fluoro, chloro, or trifluoromethyl.

15. A compound according to claim 1, selected from the group consisting of:
  5-(4-chloro-phenyl)-N-((1R,2R)-2-hydroxy-cyclohexyl)-6-(3-methoxy-propyl)-nicotinamide,
  5-(4-chloro-phenyl)-6-(2-cyclopropyl-ethyl)-N-((1R,2R)-2-hydroxy-cyclohexyl)-nicotinamide,
  N-((1R,2R)-2-hydroxy-cyclohexyl)-6-(2-pyrimidin-5-yl-ethyl)-5-(4-trifluoromethyl-phenyl)-nicotinamide,
  5-(4-chloro-phenyl)-N—((R)-2-cyclopropyl-2-hydroxy-propyl)-6-(2-pyridin-3-yl-ethyl)-nicotinamide,
  5-(4-fluoro-phenyl)-N-((1R,2R)-2-hydroxy-cyclohexyl)-6-(2-pyridin-3-yl-ethyl)-nicotinamide,
  5-(4-fluoro-phenyl)-6-[2-(5-fluoro-pyridin-2-yl)-ethyl]-N-((1R,2R)-2-hydroxy-cyclohexyl)-nicotinamide,
  5-(4-chloro-phenyl)-N-((1R,2R)-2-hydroxy-cyclohexyl)-6-(2-pyridin-3-yl-ethyl)-nicotinamide,
  5-(4-chloro-phenyl)-N-((1R,2R)-2-hydroxy-cyclohexyl)-6-(2-pyridin-2-yl-ethyl)-nicotinamide,
  N-((1R,2R)-2-hydroxy-cyclohexyl)-6-(2-pyridin-3-yl-ethyl)-5-(4-trifluoromethyl-phenyl)-nicotinamide,
  N-((1R,2R)-2-hydroxy-cyclohexyl)-6-(2-pyridin-2-yl-ethyl)-5-(4-trifluoromethyl-phenyl)-nicotinamide,
  5-(4-fluoro-phenyl)-N-((1R,2R)-2-hydroxy-cyclohexyl)-6-(2-pyridin-2-yl-ethyl)-nicotinamide, and
any pharmaceutically acceptable salt thereof.

16. A compound according to claim 1, selected from the group consisting of:
  5-(4-fluoro-phenyl)-N-((1R,2R)-2-hydroxy-cyclohexyl)-6-(2-pyridin-4-yl-ethyl)-nicotinamide,
  5-(4-fluoro-phenyl)-N-((1R,2R)-2-hydroxy-cyclohexyl)-6-(2-thiazol-2-yl-ethyl)-nicotinamide,
  5-(4-chloro-phenyl)-N-((1R,2R)-2-hydroxy-cyclohexyl)-6-(2-pyrimidin-5-yl-ethyl)-nicotinamide,
  5-(4-chloro-phenyl)-6-[2-(5-fluoro-pyridin-2-yl)-ethyl]-N-((1R,2R)-2-hydroxy-cyclohexyl)-nicotinamide,
  6-[2-(5-fluoro-pyridin-2-yl)-ethyl]-N-((1R,2R)-2-hydroxy-cyclohexyl)-5-(4-trifluoromethyl-phenyl)-nicotinamide,
  N—((R)-2-cyclopropyl-2-hydroxy-propyl)-5-(4-fluoro-phenyl)-6-(2-pyridin-4-yl-ethyl)-nicotinamide,
  N—((R)-2-cyclopropyl-2-hydroxy-propyl)-5-(4-fluoro-phenyl)-6-(2-thiazol-2-yl-ethyl)-nicotinamide,
  5-(4-chloro-phenyl)-N—((R)-2-cyclopropyl-2-hydroxy-propyl)-6-(2-pyridin-2-yl-ethyl)-nicotinamide,
  N—((R)-2-cyclopropyl-2-hydroxy-propyl)-6-(2-pyridin-2-yl-ethyl)-5-(4-trifluoromethyl-phenyl)-nicotinamide, and
any pharmaceutically acceptable salt thereof.

17. A compound according to claim 1, selected from the group consisting of:
- 5-(4-chloro-phenyl)-6-(2-cyclopropyl-ethyl)-N-((1R,2R)-2-hydroxy-cyclohexyl)-nicotinamide,
- 5-(4-chloro-phenyl)-N-((1R,2R)-2-hydroxy-cyclohexyl)-6-(2-pyridin-3-yl-ethyl)-nicotinamide,
- 5-(4-chloro-phenyl)-N-((1R,2R)-2-hydroxy-cyclohexyl)-6-(2-pyridin-2-yl-ethyl)-nicotinamide,
- N-((1R,2R)-2-hydroxy-cyclohexyl)-6-(2-pyridin-3-yl-ethyl)-5-(4-trifluoromethyl-phenyl)-nicotinamide,
- N-((1R,2R)-2-hydroxy-cyclohexyl)-6-(2-pyridin-2-yl-ethyl)-5-(4-trifluoromethyl-phenyl)-nicotinamide,
- 5-(4-fluoro-phenyl)-N-((1R,2R)-2-hydroxy-cyclohexyl)-6-(2-thiazol-2-yl-ethyl)-nicotinamide,
- 5-(4-chloro-phenyl)-6-[2-(5-fluoro-pyridin-2-yl)-ethyl]-N-((1R,2R)-2-hydroxy-cyclohexyl)-nicotinamide, and any pharmaceutically acceptable salt thereof.

18. A process for manufacturing a compound of formula I as defined in claim 1 which process comprises:
(a) coupling a compound of formula:

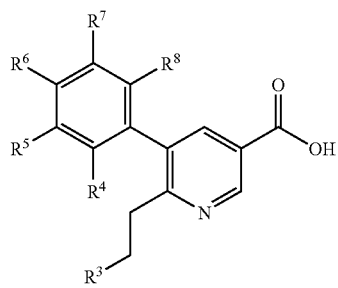

II

wherein $R^3$ to $R^8$ are as defined in claim 1, with an amine of the formula:

H—NR$^1$R$^2$   III wherein $R^1$ and $R^2$ are as defined in claim 1,
with the help of an coupling agent under basic conditions, and (b) optionally converting the resulting compound of formula I into a pharmaceutically acceptable salt thereof.

19. A process for manufacturing a compound of formula I as defined in claim 1, which process comprises:
(a) hydrogenation of a compound of formula

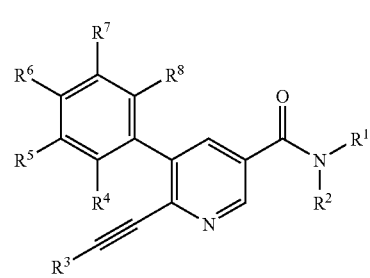

IV wherein $R^1$, $R^2$ and $R^3$ to $R^8$ are as defined in claim 1, in the presence of a catalyst, and
(b) optionally converting the resulting compound of formula I into a pharmaceutically acceptable salt thereof.

20. A pharmaceutical composition comprising a therapeutically effective amount of a compound of claim 1 and a pharmaceutically acceptable carrier.

* * * * *